United States Patent
Nakamura et al.

(10) Patent No.: US 10,562,039 B2
(45) Date of Patent: Feb. 18, 2020

(54) AUTOMATIC ANALYSIS DEVICE AND SEPARATION AND WASHING METHOD

(71) Applicants: JEOL Ltd., Tokyo (JP); Fujirebio Inc., Tokyo (JP)

(72) Inventors: Mizuki Nakamura, Tokyo (JP); Tomohiro Endo, Tokyo (JP); Kazuyuki Oguri, Tokyo (JP)

(73) Assignees: JEOL Ltd., Tokyo (JP); Fujirbio Inc., Tokyo (JP)

( * ) Notice: Subject to any disclaimer, the term of this patent is extended or adjusted under 35 U.S.C. 154(b) by 121 days.

(21) Appl. No.: 15/520,228

(22) PCT Filed: Sep. 29, 2015

(86) PCT No.: PCT/JP2015/077604
§ 371 (c)(1),
(2) Date: Apr. 19, 2017

(87) PCT Pub. No.: WO2016/063690
PCT Pub. Date: Apr. 28, 2016

(65) Prior Publication Data
US 2017/0312756 A1    Nov. 2, 2017

(30) Foreign Application Priority Data
Oct. 24, 2014   (JP) ................. 2014-217310

(51) Int. Cl.
*B03C 1/02* (2006.01)
*G01B 11/25* (2006.01)
(Continued)

(52) U.S. Cl.
CPC .............. *B03C 1/02* (2013.01); *B03C 1/00* (2013.01); *G01B 11/25* (2013.01); *G01B 11/306* (2013.01);
(Continued)

(58) Field of Classification Search
None
See application file for complete search history.

(56) References Cited

U.S. PATENT DOCUMENTS 5,147,529 A * 9/1992 Lee .................. B03C 1/01
                                                     210/695
5,705,062 A   1/1998 Knobel
(Continued)

FOREIGN PATENT DOCUMENTS

EP   0502638 A2   9/1992
EP   0644425 A1   3/1995
(Continued)

OTHER PUBLICATIONS

Extended European Search Report issued in European Patent Application No. EP15852419.9 dated Jun. 5, 2018.

*Primary Examiner* — Kathryn Wright
(74) *Attorney, Agent, or Firm* — The Webb Law Firm

(57) ABSTRACT

An automatic analysis device and method having a BF separation process, wherein the width in a container conveyance direction of a surface facing a reaction container of a magnet for preliminary magnetic collection of a first magnetic generation part (32p) is set to have a length including a region for housing a liquid sample of the reaction container conveyed to a magnetic collection position of the first magnetic generation part. An end in the container conveyance direction of a surface facing the reaction container of a magnet for regular magnetic collection of a second magnetic generation part (32m) is designed to be close to the center of the region for housing the liquid sample of the reaction container conveyed to a magnetic collection position of the second magnetic generation part.

6 Claims, 14 Drawing Sheets

(51) Int. Cl.
  *G01B 11/30* (2006.01)
  *G01N 21/89* (2006.01)
  *G01N 35/00* (2006.01)
  *G01N 35/02* (2006.01)
  *G01N 35/10* (2006.01)
  *B03C 1/00* (2006.01)
  *G01N 35/04* (2006.01)
  *G01N 33/543* (2006.01)
  *G01N 1/34* (2006.01)
  *G01N 1/40* (2006.01)

(52) U.S. Cl.
  CPC ... *G01N 21/8901* (2013.01); *G01N 33/54333* (2013.01); *G01N 35/0098* (2013.01); *G01N 35/0099* (2013.01); *G01N 35/02* (2013.01); *G01N 35/04* (2013.01); *G01N 35/1011* (2013.01); *G01N 1/34* (2013.01); *G01N 1/405* (2013.01); *G01N 35/025* (2013.01); *G01N 2035/00564* (2013.01); *G01N 2035/1088* (2013.01)

(56) References Cited

U.S. PATENT DOCUMENTS

| | | |
|---|---|---|
| 5,741,708 A | 4/1998 | Carey et al. |
| 5,985,671 A | 11/1999 | Leistner et al. |
| 6,143,578 A * | 11/2000 | Bendele ............ B03C 1/0332 |
| | | 209/214 |
| 2004/0265903 A1 | 12/2004 | Mueller et al. |
| 2008/0206099 A1 | 8/2008 | Aruga et al. |
| 2012/0149127 A1 | 6/2012 | Toyoshima et al. |
| 2013/0323758 A1 | 12/2013 | Oguri et al. |

FOREIGN PATENT DOCUMENTS

| | | |
|---|---|---|
| EP | 1964613 A2 | 9/2008 |
| EP | 2466314 A2 | 6/2012 |
| JP | 458157 A | 2/1992 |
| JP | 10504389 A | 4/1998 |
| JP | 2003227838 A | 8/2003 |
| JP | 2004535591 A | 11/2004 |
| JP | 201032215 A | 2/2010 |
| JP | 2012173180 A | 9/2012 |

* cited by examiner

| BF SEPARATION | RATIO OF HOW MUCH PARTICLES REMAIN [%] |
|---|---|
| 1 | 90.0% |
| 2 | 73.6% |
| 3 | 64.2% |
| 4 | 63.4% |
| 5 | 76.7% |
| Average | 73.6% |
| CV | 14.74% |

| BF SEPARATION | RATIO OF HOW MUCH PARTICLES REMAIN [%] |
|---|---|
| 1 | 91.5% |
| 2 | 90.8% |
| 3 | 91.4% |
| 4 | 90.6% |
| 5 | 90.8% |
| Average | 91.1% |
| CV | 0.45% |

AUTOMATIC ANALYSIS DEVICE AND SEPARATION AND WASHING METHOD

CROSS-REFERENCE TO RELATED APPLICATIONS

This application is the United States national phase of International Application No. PCT/JP2015/077604 filed Sep. 29, 2015, and claims priority to Japanese Patent Application No. 2014-217310 filed Oct. 24, 2014, the disclosures of which are hereby incorporated in their entirety by reference.

TECHNICAL FIELD

The present invention relates to an automatic analysis device, particularly, an automatic analysis device including solid-phase magnetic particles and a separation and washing method.

BACKGROUND ART

Automatic analysis devices are used for tests in various different fields, such as for an immunological test, a biochemical test, or a blood transfusion test to analyze many samples. Automatic analysis devices quickly and highly accurately analyze an intended substance among many components contained in each sample.

Automatic analysis devices include an immune analysis device that quantitatively or qualitatively detects, through immunoreaction, an intended substance (such as antigen or antibody) contained in a sample (such as serum, blood plasma, or urine). An immune analysis device includes a system for bound-free (BF) separation performed to separate an intended substance in the sample, which is to be analyzed, from a reaction solution and wash the intended substance using a reagent in which an antigen or an antibody that reacts on the intended substance in the sample is combined with a solid phase (such as a magnetic particle).

For BF separation, a nozzle of an automatic analysis device that uses magnetic particles is inserted into a reaction solution in a reaction vessel and caused to suck the reaction solution in the reaction vessel. At this time, the reaction solution is sucked while the magnetic particles are temporarily attracted to (magnetically collected on) an inner wall surface of the reaction vessel by magnets disposed outside the reaction vessel so that the magnetic particles that form immune complexes contained in the reaction solution are not sucked. Thus, only magnetic particles that are bound to an intended substance to form immune complexes are left in the reaction vessel and other unreacted sample-derived components or the like are removed through the sucked solution. Thereafter, a washing liquid is discharged and sucked through the nozzle to and from the reaction vessel, so that the magnetic particles in the reaction vessel are washed. The number of times the BF separation operation is performed is determined depending on the conditions of an analysis of an intended substance.

Various different types of BF separation mechanism for an automatic analysis device have been developed to efficiently perform the BF separation. A disclosed example of a device performs two steps of magnetic collection on a reaction vessel using one magnet disposed on one side surface of the reaction vessel (see, for example, PTL 1). In addition, a disclosed example of a device that is equipped with a BF separation mechanism performs two steps of magnetic collection using first magnetic means and second magnetic means before performing BF separation (see, for example, PTL 2).

CITATION LIST

Patent Literature

PTL 1: Japanese Unexamined Patent Application Publication No. 4-58157
PTL 2: Japanese Unexamined Patent Application Publication No. 2003-227838

SUMMARY OF INVENTION

Technical Problem

The magnetic particles in an automatic analysis device are particles having a diameter of approximately 1 μm to 10 μm. The magnetic particles form immune complexes and float while being suspended in the reaction solution. A BF separation operation involves a time lag from when a magnet approaches a reaction vessel until when magnetic particles are completely attracted to the inner wall surface of the reaction vessel. This time lag differs depending on factors such as the particle diameter of particles, the magnetic force of the magnet, or the shape of the reaction vessel but falls within a range of approximately several seconds to approximately ten-odd seconds. The magnetic particles that have not yet been attracted to the inner wall surface of the reaction vessel may thus be sucked together with the reaction solution if the nozzle is inserted into the reaction vessel immediately after the magnetic collection and performs a suction operation of the reaction solution before the magnetic collection is completely performed.

To address this situation, a preliminary magnetic collection step, in which the magnetic particles contained in the reaction solution are attracted to the inner wall surface of the reaction vessel in advance, is provided as a preliminary step for transition to an actual BF washing step. This step allows the magnetic particles to be preliminarily attracted to the inner wall surface of the reaction vessel in a sufficiently long period of the preliminary magnetic collection step before transition to an actual BF washing step (main magnetic collection). In the BF washing step, the magnetic particles magnetically collected in advance are held and an additional magnetic collection is performed. Thus, the washing step, for which the BF washing step is intended, can take a sufficiently long time without the need of waiting until the magnetic particles are magnetically collected.

Existing automatic analysis devices take following measures to magnetically collect magnetic particles in a reaction vessel during BF separation and washing. PTL 1 discloses a method including two steps of magnetic collection using a single magnet and a method including preliminary magnetic collection and main magnetic collection using two magnets of the same shape. PTL 2 discloses an analysis device including a BF separation mechanism in which multiple magnets are disposed on the side surface of the reaction vessel at different levels lowered stepwise. These devices fail to fully collect magnetic particles in the reaction solution within a predetermined time required for magnetic collection. These devices thus allow some amount of magnetic particles to flow out of the reaction vessel during a washing operation and cause problems of varying analysis results and reducing analytical sensitivity. Specifically, the shapes of magnets included in existing devices are appropriate for neither preliminary magnetic collection nor main magnetic collection.

The present invention was made in consideration of the above-described circumstances and aims to provide a device that reduces the amount of magnetic particles flowing out during a washing operation in a BF separation step involving preliminary magnetic collection and main magnetic collection.

Solution to Problem

To solve the above-described problem, an aspect of an automatic analysis device according to the invention is an automatic analysis device that analyzes an intended substance contained in a sample using a reagent containing magnetic particles. The automatic analysis device includes a vessel transport portion, a first magnetic generation part, a second magnetic generation part, and a separation and washing portion.

In the vessel transport portion, vessels holding a liquid sample containing the sample and the reagent containing the magnetic particles are disposed. The vessel transport portion transports the vessels along a path.

The first magnetic generation part is disposed on the path and includes at least one preliminary-magnetic-collection magnet that magnetically collects the magnetic particles in the liquid sample inside each of the vessels that has been transported to a magnetic collection position of the first magnetic generation part.

The second magnetic generation part is disposed on the path downstream from the first magnetic generation part. The second magnetic generation part includes at least one main-magnetic-collection magnet that magnetically collects the magnetic particles in the liquid sample that have been magnetically collected by the first magnetic generation part. The liquid sample is held inside each vessel that has been transported to a magnetic collection position of the second magnetic generation part.

The separation and washing portion separates a component other than the magnetic particles and washes an inside of each vessel while the magnetic particles are magnetically collected inside the vessel by the second magnetic generation part.

A surface of the preliminary-magnetic-collection magnet of the first magnetic generation part facing the vessels has a width in a vessel transport direction that is as long as to cover an effective area of each vessel that has been transported to the magnetic collection position of the first magnetic generation part. A surface of the main-magnetic-collection magnet of the second magnetic generation part facing the vessels has an end portion in the vessel transport direction that is located adjacent to a center of the effective area of each vessel that has been transported to the magnetic collection position of the second magnetic generation part.

An aspect of a separation and washing method according to the invention is a separation and washing method for separating and washing a component containing magnetic particles with an automatic analysis device that analyzes an intended substance contained in a sample using a reagent containing magnetic particles.

In the separation and washing method, vessels each holding a liquid sample containing the sample and the reagent containing the magnetic particles are transported along a path using a vessel transport portion in which the vessels are disposed.

In addition, the magnetic particles in the liquid sample inside each of the vessels that has been transported to a magnetic collection position of a first magnetic generation part, disposed on the path and including a preliminary-magnetic-collection magnet, are magnetically collected by the first magnetic generation part.

In addition, the magnetic particles in the liquid sample that have been magnetically collected by the first magnetic generation part inside each of the vessels that has been transported to a magnetic collection position of a second magnetic generation part are magnetically collected by the second magnetic generation part, the second magnetic generation part being disposed on the path downstream from the first magnetic generation part, the second magnetic generation part including a main-magnetic-collection magnet.

A component containing the magnetic particles is separated and an inside of each vessel is washed using a separation and washing portion while the magnetic particles are magnetically collected inside the vessel by the second magnetic generation part.

A surface of the preliminary-magnetic-collection magnet of the first magnetic generation part facing the vessels has a width in a vessel transport direction that is as long as to cover an area of each vessel that has been transported to the magnetic collection position of the first magnetic generation part, the area holding the liquid sample.

A surface of the main-magnetic-collection magnet of the second magnetic generation part facing the vessels has an end portion in the vessel transport direction that is located adjacent to a center of the area of each vessel that has been transported to the magnetic collection position of the second magnetic generation part, the area holding the liquid sample.

Advantageous Effects of Invention

At least one aspect of the present invention is capable of reducing the amount of magnetic particles flowing out through a washing operation in a BF separation step involving preliminary magnetic collection and main magnetic collection.

BRIEF DESCRIPTION OF DRAWINGS

FIG. 12A shows lines of the magnetic force viewed from above the first magnetic generation part and FIG. 12B shows lines of the magnetic force viewed from a side of the first magnetic generation part.

FIG. 20A illustrates an image of magnetically collected magnetic particles remaining when only the first magnetic generation part is used, FIG. 20B illustrates an image of magnetically collected magnetic particles remaining when only the second magnetic generation part is used, and FIG. 20C illustrates an image of magnetically collected magnetic particles remaining when the first magnetic generation part and the second magnetic generation part are used.

DESCRIPTION OF EMBODIMENTS

Referring now to the attached drawings, examples of forms in which the present invention is embodied are described below. Throughout the drawings, the same components are denoted with the same reference symbols and are not described redundantly.

Embodiments described below each exemplarily disclose an immune analysis device, but the present invention is not limited to an immune analysis device. The present invention is also applicable to, for example, a nucleic acid detecting/measuring device that solidifies and attaches a nucleic acid probe to a magnetic particle and captures nucleic acid (DNA or RNA) in the sample. The present invention is applicable to all the automatic analysis devices including a BF separation mechanism using magnetic particles.

<1. First Embodiment>
[Summary of Automatic Analysis Device]

Figure 1:
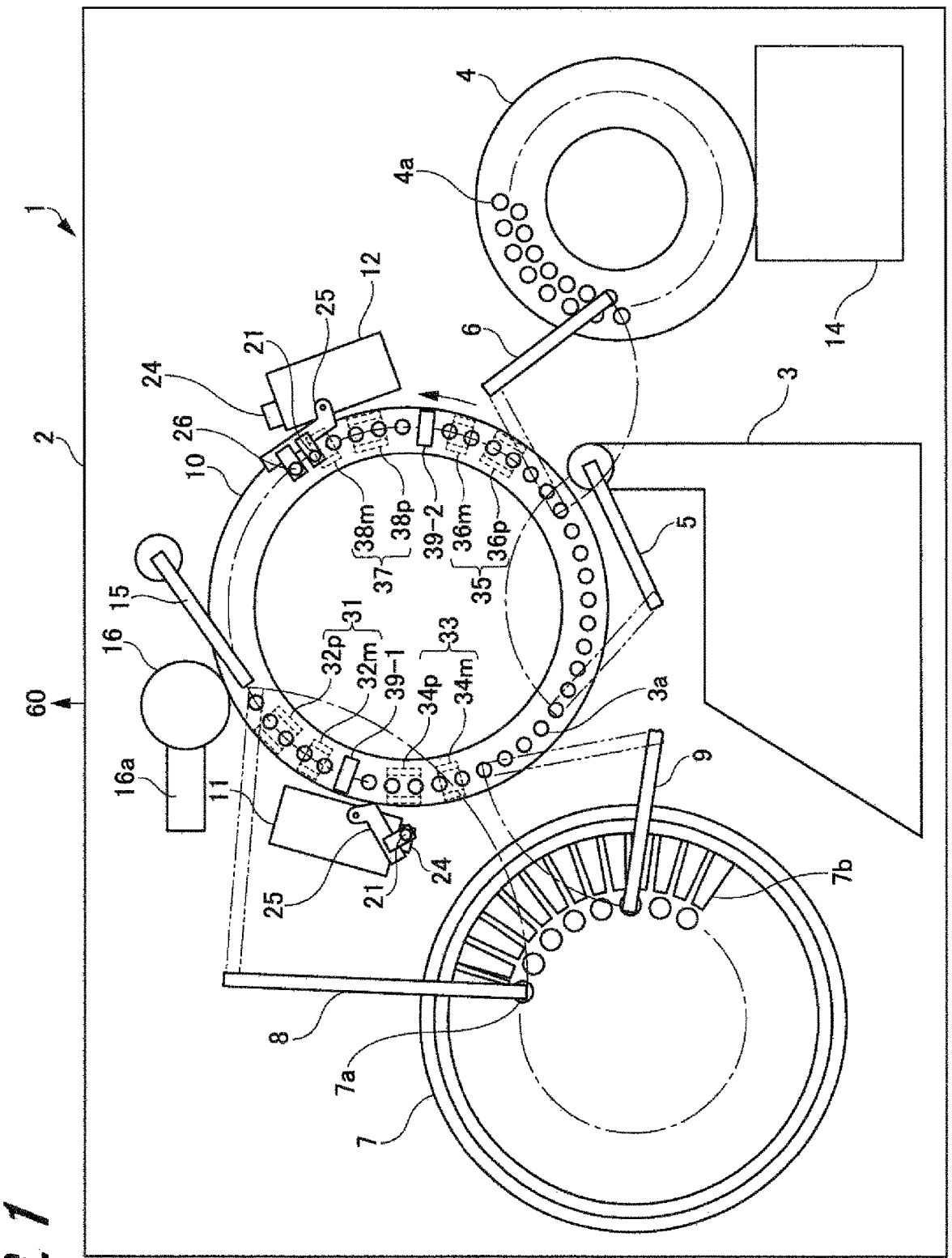
FIG. 1 is a schematic diagram of a configuration of an automatic analysis device according to a first embodiment of the invention.

FIG. 1 is a schematic diagram of a configuration of an automatic analysis device according to a first embodiment of the present invention.

An automatic analysis device 1 illustrated in FIG. 1 is a form obtained by applying the present invention to an immune analysis device that detects or measures objects such as an antigen or an antibody in the sample through an immune analysis. The automatic analysis device 1 includes a measuring device 2 and a controlling device 60 (FIG. 3), which controls the entirety of the automatic analysis device 1 including the measuring device 2 and analyzes measurement data output from the measuring device 2.

The automatic analysis device 1, which is an immune analysis device, performs highly sensitive measurement by, for example, chemiluminescent enzyme immunoassay (CLEIA). CLEIA includes, as main steps, a reaction step, in which an intended substance (antigen or antibody) in the sample is caused to react with a reagent in a reaction vessel, a separation step (BF separation), in which a reacted (bound) substance and an unreacted (free) substance in the reaction vessel are separated from each other, and a light measurement step in which an amount of light resulting from a reaction between a chemiluminescent substrate and an immune complex is measured, the immune complex being produced from a reaction between each reagent and the intended substance in the sample.

[Measurement System of Automatic Analysis Device]

The measuring device 2 mainly includes a reaction vessel supply unit 3, a sample stand unit 4, a reaction vessel transport unit 5, a sample pipetting unit 6, a reagent cooling unit 7, a first reagent pipetting unit 8, a second reagent pipetting unit 9, an immuno-enzyme reaction unit 10, a first BF separation unit 11, a second BF separation unit 12, a substrate liquid cooling device 14, a vessel transfer arm 15, and a luminescence measurement unit 16.

The reaction vessel supply unit 3 houses multiple reaction vessels (cuvettes) 3a and provides the multiple reaction vessels 3a one by one to a transfer position. Each of the reaction vessels 3a provided to the transfer position is transported to the immuno-enzyme reaction unit 10 by the reaction vessel transport unit 5. A sample and a predetermined reagent are fed to each of the reaction vessels 3a transported to the immuno-enzyme reaction unit 10.

The reaction vessel transport unit 5 includes an arm, which rises and lowers vertically and freely rotates around a vertical line that passes through its base end portion, and a holding portion, disposed at a far end portion of the arm. The reaction vessel transport unit 5 holds each reaction vessel 3a fed to a feed position of the reaction vessel supply unit 3 using the holding portion and rotates the arm to transport the reaction vessel 3a to a predetermined position of the immuno-enzyme reaction unit 10 at a predetermined timing.

The sample stand unit 4 includes a turntable having a shape of a substantially cylindrical tubular vessel having one end in the axial direction open. The sample stand unit 4 houses multiple sample vessels 4a. Each sample vessel 4a holds a sample, such as blood or urine, taken from a subject. The multiple sample vessels 4a are arranged at predetermined intervals in the circumferential direction of the sample stand unit 4. The sample stand unit 4 is supported by a driving mechanism, not illustrated, so as to be rotatable in the circumferential direction. The sample stand unit 4 is rotated by the driving mechanism, not illustrated, in the circumferential direction at each predetermined angle range at a predetermined speed. In the example illustrated in FIG.

1, the sample vessels 4a are arranged in the circumferential direction of the sample stand unit 4 in two rows, which are spaced apart from each other at a predetermined distance in the radial direction of the sample stand unit 4. Examples usable as a sample may include a sample diluted by a predetermined dilution.

The sample pipetting unit 6 includes an arm and a probe. The arm rises and lowers vertically and freely rotates around a vertical line passing through its base end portion. The probe is disposed at a far end portion of the arm. The sample pipetting unit 6 sucks, through the probe, the sample inside each sample vessel 4a shifted to a predetermined position of the sample stand unit 4 and rotates the arm to pipette the sample into a reaction vessel 3a positioned at a predetermined position of the immuno-enzyme reaction unit 10 at a predetermined timing.

Similarly to the sample stand unit 4, the reagent cooling unit 7 also includes a turntable having a shape of a substantially cylindrical tubular vessel having one end in the axial direction open. The reagent cooling unit 7 is supported by a driving mechanism, not illustrated, so as to be rotatable in the circumferential direction. The reagent cooling unit 7 is rotated by the driving mechanism, not illustrated, forward or backward in the circumferential direction by each predetermined angle range at a predetermined speed.

The reagent cooling unit 7 houses first reagent vessels 7a and second reagent vessels 7b. The first reagent vessels 7a and the second reagent vessels 7b are arranged on the reagent cooling unit 7 in the circumferential direction at predetermined intervals. Each first reagent vessel 7a holds a first reagent, an example of which is a magnetic reagent containing magnetic particles that react with an intended substance (for example, antigen) in the sample. Each second reagent vessel 7b holds a second reagent, an example of which is a labeling reagent (enzyme antibody) that reacts with a reacted product in which the magnetic reagent is bound with an intended substance (for example, antigen) in the sample. The inside of the reagent cooling unit 7 is kept at a predetermined temperature by a cooling system, not illustrated. Thus, the first reagent (magnetic reagent) held in each first reagent vessel 7a and the second reagent (labeling reagent) held in each second reagent vessel 7b are cooled at the predetermined temperature.

The first reagent pipetting unit 8 includes an arm and a probe. The arm rises and lowers vertically and freely rotates around a vertical line passing through its base end portion. The probe is disposed at a far end portion of the arm. The first reagent pipetting unit 8 sucks, through the probe, the first reagent (magnetic reagent) inside each first reagent vessel 7a shifted to a predetermined position of the reagent cooling unit 7 and rotates the arm to pipette the first reagent into the reaction vessel 3a positioned at a predetermined position of the immuno-enzyme reaction unit 10 at a predetermined timing.

The second reagent pipetting unit 9 has a similar configuration as that of the first reagent pipetting unit 8. The second reagent pipetting unit 9 sucks, through the probe, the second reagent (labeling reagent) inside each second reagent vessel 7b shifted to a predetermined position of the reagent cooling unit 7 and rotates the arm to pipette the second reagent into the reaction vessel 3a positioned at a predetermined position of the immuno-enzyme reaction unit 10 at a predetermined timing.

In the immuno-enzyme reaction unit 10, each of the reaction vessels 3a arranged in the circumferential direction allows the sample and a predetermined reagent corresponding to an intended analysis category to cause an immuno-reaction and an immune complex resulting from this immuno-reaction and a chemiluminescent substrate to cause an enzyme reaction. The immuno-enzyme reaction unit 10 also serves as a thermostat that keeps the temperature of the reaction vessel 3a constant.

Similarly to the sample stand unit 4, the immuno-enzyme reaction unit 10 (an example of a vessel transport portion) includes a turntable having a shape of a substantially cylindrical tubular vessel having one end in the axial direction open. The immuno-enzyme reaction unit 10 is supported by a driving mechanism, not illustrated, so as to be rotatable in the circumferential direction. The immuno-enzyme reaction unit 10 is rotated by the driving mechanism, not illustrated, in the circumferential direction by each predetermined angle range at a predetermined speed. An example used as the mechanism that drives the turntable to rotate is a stepping motor. Here, the immuno-enzyme reaction unit 10 rotates counterclockwise (in the direction of arrow). In the example illustrated in FIG. 1, the reaction vessels 3a are arranged in the circumferential direction of the immuno-enzyme reaction unit 10 in a single row at a predetermined interval. Alternatively, a row of reaction vessels 3a for the first reagent, described below, and a row of reaction vessels 3a for the second reagent, described below, may be disposed at a predetermined distance away from each other in the radial direction (see FIG. 24).

When the first reagent pipetting unit 8 pipettes a magnetic reagent into each reaction vessel 3a holding the sample, the immuno-enzyme reaction unit 10 stirs a liquid mixture (liquid sample) containing the magnetic reagent and the sample using a stirring system, not illustrated, and allows the magnetic reagent and the intended substance (for example, antigen) in the sample to cause immunoreactions for a predetermined time period (primary immunoreaction). Subsequently, the immuno-enzyme reaction unit 10 moves the reaction vessel 3a to a first magnetic collection mechanism (first-half magnetic collection mechanism 31 and second-half magnetic collection mechanism 33) to magnetically collect a reacted product, in which the intended substance and the magnetic reagent are bound, using a magnetic force. In this state, the inside of the reaction vessel 3a is washed and an unreacted substance that has not reacted with the magnetic reagent is removed (primary BF separation).

The first magnetic collection mechanism is fixed at a position corresponding to the first BF separation unit 11, disposed near the outer circumferential portion of the immuno-enzyme reaction unit 10. The first magnetic collection mechanism includes a first-half magnetic collection mechanism 31 and a second-half magnetic collection mechanism 33. The first-half magnetic collection mechanism 31 includes a first magnetic generation part 32p and a second magnetic generation part 32m, disposed downstream from the first magnetic generation part 32p in a vessel transport direction. The second-half magnetic collection mechanism 33 includes a first magnetic generation part 34p and a second magnetic generation part 34m, disposed downstream from the first magnetic generation part 34p in the vessel transport direction. A stirring system 39-1 is disposed between the first-half magnetic collection mechanism 31 and the second-half magnetic collection mechanism 33. The magnetic generation parts and the stirring system 39-1 are arranged in the circumferential direction at predetermined intervals corresponding to the pitch at which the reaction vessels 3a are transported.

Figure 2:
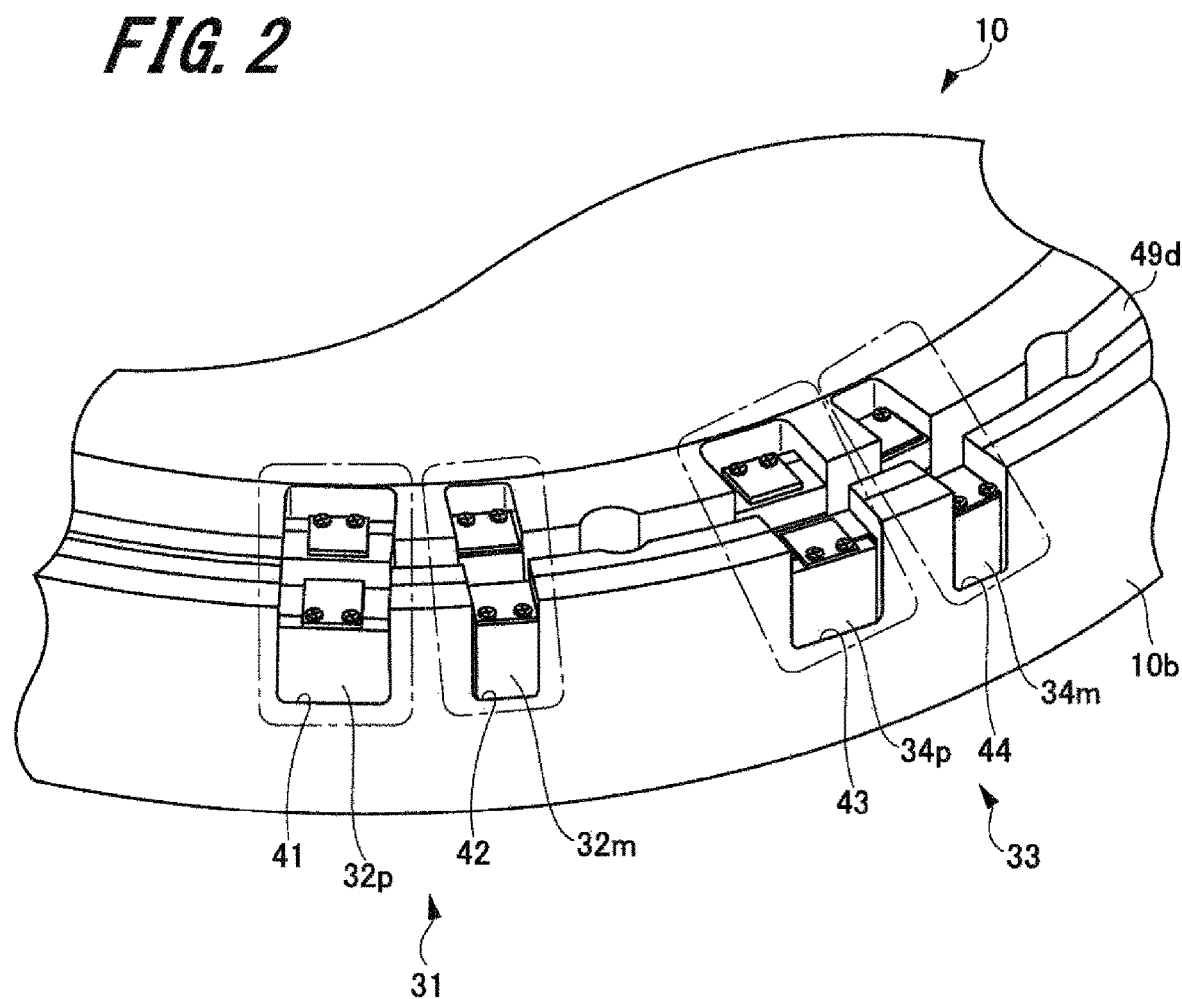
FIG. 2 is a schematic perspective view of the automatic analysis device illustrated in FIG. 1 from which an upper layer of a turntable of an immuno-enzyme reaction unit is removed.

Referring now to FIG. 2, the turntable of the immuno-enzyme reaction unit 10 is described.

FIG. 2 is a schematic perspective view of the automatic analysis device 1 illustrated in FIG. 1 from which the upper layer of the turntable of the immuno-enzyme reaction unit 10 is removed.

The turntable of the immuno-enzyme reaction unit 10 includes two layers, that is, a fixed lower layer 10b and a rotatable upper layer (not illustrated). As illustrated in FIG. 2, the first-half magnetic collection mechanism 31 and the second-half magnetic collection mechanism 33 of the first magnetic collection mechanism are disposed on the lower layer 10b of the turntable. The reaction vessels 3a (see FIG. 1) are disposed on the upper layer of the turntable. The lower layer 10b of the turntable of the immuno-enzyme reaction unit 10 has an annular groove 49d extending in the circumferential direction, on the path along which the reaction vessels 3a pass. The lower layer 10b of the turntable of the immuno-enzyme reaction unit 10 also has storage grooves 41, 42, 43, and 44, extending perpendicularly to the groove 49d.

Figure 7:
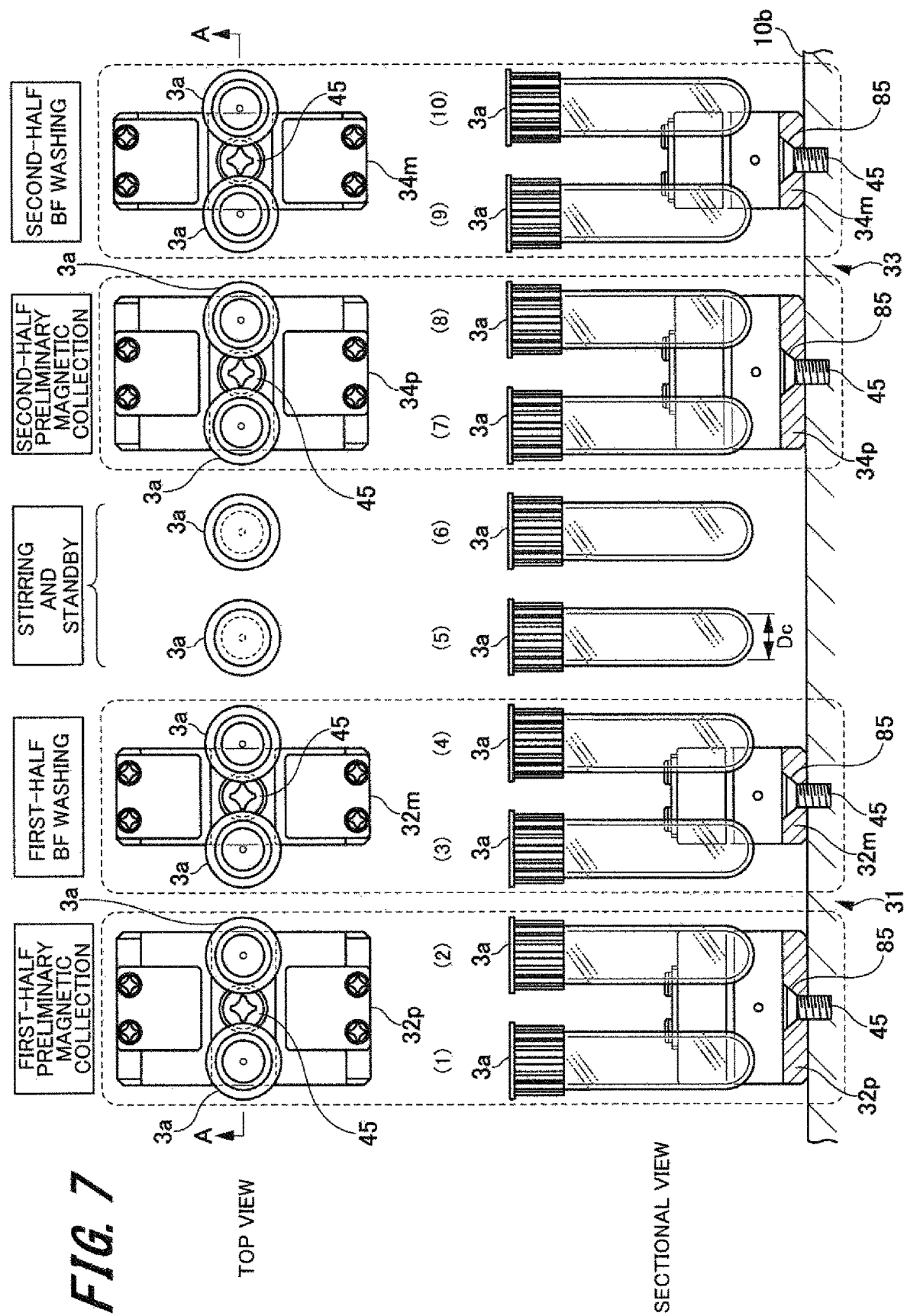
FIG. 7 illustrates, in a schematic top view and a schematic sectional view, the positional relationship between the reaction vessels and the magnetic generation parts during the BF separation step.

The first magnetic generation part 32p and the second magnetic generation part 32m of the first-half magnetic collection mechanism 31 are respectively fitted into (held in) the storage groove 41 and the storage groove 42 and disposed on the path of the reaction vessels 3a. Similarly, the first magnetic generation part 34p and the second magnetic generation part 34m of the second-half magnetic collection mechanism 33 are respectively fitted into (held in) the storage groove 43 and the storage groove 44 and disposed on the path of the reaction vessels 3a. As illustrated in FIG. 7, described below, for example, each of the first and second magnetic generation parts 32p, 32m, 34p, and 34m has a through hole 85 (see FIG. 10, described below). A male screw 45 is screwed onto a female screw, formed in the lower layer 10b of the turntable, through the through hole 85 of each magnetic generation part. Each magnetic generation part is thus fixed to the lower layer 10b of the turntable. The first and second magnetic generation parts 32p, 32m, 34p, and 34m of the first-half magnetic collection mechanism 31 and the second-half magnetic collection mechanism 33 each produce magnetism to magnetically collect magnetic particles and reacted products containing the magnetic particles inside each reaction vessel 3a that has been transported thereto along the path.

As described below, the first magnetic generation parts 32p and 34p are used for preliminary magnetic collection and the second magnetic generation parts 32m and 34m are used for main magnetic collection during BF washing. The first magnetic generation parts 32p and 34p and the second magnetic generation parts 32m and 34m have different dimensions in the cross direction, which is parallel to the tangential direction of the immuno-enzyme reaction unit 10. The reason for this will be described below. In the following description of BF separation, magnetic particles and reacted products containing the magnetic particles are collectively referred to as "magnetic particles" in some cases.

FIG. 1 is described again. The first BF separation unit 11 (an example of a separation and washing portion) includes an arm 25, a nozzle 21 attached to the arm 25, and a washing bath 24. The arm 25 rises and lowers vertically and freely rotates around a vertical line passing through its base end portion. The arm 25 moves the nozzle 21 between the reaction vessel 3a positioned at a primary BF separation position of the immuno-enzyme reaction unit 10 and the washing bath 24 positioned at a nozzle washing position near the first BF separation unit 11. In this embodiment, the primary BF separation is divided into first-half and second-half processes. The first-half process is performed by the first-half magnetic collection mechanism 31 and the second-half process is performed by the second-half magnetic collection mechanism 33. The nozzle 21 discharges a washing liquid into the reaction vessel 3a holding the sample and the magnetic reagent at the primary BF separation position and sucks the washing liquid from the reaction vessel 3a to wash the reaction vessel 3a and remove an unreacted substance that did not react with the magnetic reagent (BF washing).

When each reaction vessel 3a is transported to the primary BF separation position, the first BF separation unit 11 performs primary BF separation. In the primary BF separation and the BF washing, a reacted product, in which an intended substance in the sample and the magnetic reagent are bound, is magnetically collected in the reaction vessel 3a. When the primary BF separation is finished, the arm 25 moves the nozzle 21 to the nozzle washing position at which the washing bath 24 is disposed. In the example illustrated in FIG. 1, the first BF separation unit 11 moves each reaction vessel 3a to the primary BF separation position or the nozzle washing position using the single arm 25. However, arms may be individually provided for the first-half magnetic collection mechanism 31 and the second-half magnetic collection mechanism 33.

After the primary BF separation, the second reagent pipetting unit 9 pipettes a labeling reagent into the reaction vessel 3a in which a reacted product remains. Then, the immuno-enzyme reaction unit 10 stirs a liquid mixture (liquid sample), containing the labeling reagent and the reacted product, using a stirring system, not illustrated, and allows the reacted product and the labeling reagent to cause an immunoreaction (secondary immunoreaction) for a predetermined time period. Subsequently, the immuno-enzyme reaction unit 10 moves the reaction vessel 3a to the second magnetic collection mechanism to magnetically collect an immune complex, in which the reacted product and the labeling reagent are bound, using a magnetic force. In this state, the inside of the reaction vessel 3a is washed and the unreacted substance that has not reacted with the labeling reagent is removed (secondary BF separation).

The second magnetic collection mechanism has a configuration similar to that of the first magnetic collection mechanism. The second magnetic collection mechanism is fixed in a position corresponding to the second BF separation unit 12, disposed near the outer circumferential portion of the immuno-enzyme reaction unit 10. Similarly to the first magnetic collection mechanism, the second magnetic collection mechanism includes a first-half magnetic collection mechanism 35 and a second-half magnetic collection mechanism 37. The first-half magnetic collection mechanism 35 includes a first magnetic generation part 36p and a second magnetic generation part 36m, disposed downstream from the first magnetic generation part 36p in the vessel transport direction. The second-half magnetic collection mechanism 37 includes a first magnetic generation part 38p and a second magnetic generation part 38m, disposed downstream from the first magnetic generation part 38p in the vessel transport direction. A stirring system 39-2 is disposed between the first-half magnetic collection mechanism 35 and the second-half magnetic collection mechanism 37. The magnetic generation parts and the stirring system 39-2 are arranged in the circumferential direction at predetermined intervals corresponding to the pitch at which the reaction vessels 3a are transported.

Similarly to the first magnetic collection mechanism, the first-half magnetic collection mechanism 35 and the second-half magnetic collection mechanism 37 of the second magnetic collection mechanism are disposed on the lower layer 10b (see FIG. 2) of the turntable. Although not illustrated, the lower layer 10b of the turntable of the immuno-enzyme reaction unit 10 has other four storage grooves 41 to 44, each extending perpendicularly to the groove 49d, as in the case of the first magnetic collection mechanism. The first magnetic generation part 36p and the second magnetic generation part 36m of the first-half magnetic collection mechanism 35 are respectively fitted into (held in) the storage groove 41 and the storage groove 42 and disposed on the path of the reaction vessels 3a. Similarly, the first magnetic generation part 38p and the second magnetic generation part 38m of the second-half magnetic collection mechanism 37 are respectively fitted into (held in) the storage groove 43 and the storage groove 44 and disposed on the path of the reaction vessels 3a. The magnetic generation parts of the first-half magnetic collection mechanism 35 and the second-half magnetic collection mechanism 37 each produce magnetism to magnetically collect magnetic particles and reacted products containing the magnetic particles inside each reaction vessel 3a that has been transported thereto along the path.

FIG. 1 is described again. The second BF separation unit 12 (an example of a separation and washing portion) has a similar configuration as that of the first BF separation unit 11. The second BF separation unit 12 is disposed at a predetermined distance away from the first BF separation unit 11 in the circumferential direction. The arm 25 rises and lowers vertically and freely rotates around a vertical line that passes through its base end portion. The arm 25 moves the nozzle 21 between the reaction vessel 3a positioned at a secondary BF separation position of the immuno-enzyme reaction unit 10 and the washing bath 24, positioned at a nozzle washing position near the second BF separation unit 12. In this embodiment, the secondary BF separation is divided into first-half and second-half processes. The first-half process is performed by the first-half magnetic collection mechanism 35 and the second-half process is performed by the second-half magnetic collection mechanism 37. The nozzle 21 discharges a washing liquid into the reaction vessel 3a holding the labeling reagent at the secondary BF separation position and sucks the washing liquid from the reaction vessel 3a to wash the reaction vessel 3a and remove a remnant unreacted substance that did not react with the labeling reagent (BF washing).

The second BF separation unit 12 performs secondary BF separation when each reaction vessel 3a is transported to the secondary BF separation position. During the secondary BF separation and the BF washing, an immune complex in which the labeling reagent and the reacted product, consisting of an intended substance in the sample and the magnetic reagent, are bound is magnetically collected in the reaction vessel 3a. When the secondary BF separation is finished, the arm 25 moves the nozzle 21 to the nozzle washing position at which the washing bath 24 is disposed. Similarly to the first BF separation unit 11, the second BF separation unit 12 moves the reaction vessel 3a using the single arm 25 between the secondary BF separation position and the nozzle washing position. However, arms may be individually provided for the first-half magnetic collection mechanism 35 and the second-half magnetic collection mechanism 37.

Here, the nozzle 21 and the washing bath 24 are described. The first BF separation unit 11 and the second BF separation unit 12 are described collectively.

The nozzle 21 includes, for example, a discharge nozzle (example of discharge unit), which discharges a washing liquid, and a suction nozzle (example of suction unit), which sucks the washing liquid. The discharge nozzle and the suction nozzle are disposed so as touch each other in a direction parallel to the axial direction. The discharge nozzle has a tubular shape and has an opening (discharge port) at its lower end. The suction nozzle has a tubular shape that is longer than the discharge nozzle in the axial direction. The suction nozzle has an opening (suction port) at its lower end. The lower end of the nozzle 21 is a portion from which the nozzle 21 enters the reaction vessel 3a or the washing bath 24.

The washing bath 24 has a substantially quadrangular prism or cylinder shape having an opening at its top portion. The washing bath 24 is capable of storing the washing liquid discharged from the nozzle 21 inserted thereinto from its top portion during the nozzle washing. The washing bath 24 has an exhaust port in it bottom surface. The stored washing liquid is discharged through the exhaust port.

FIG. 1 is described again. A substrate solution pipetting unit 26 is also attached to the arm 25 of the second BF separation unit 12. The substrate solution pipetting unit 26 is disposed at a position further from the rotation shaft of the arm 25 than is the position of the nozzle 21. The substrate solution pipetting unit 26 is connected to the substrate liquid cooling device 14, which holds and cools a substrate solution, with a tube, not illustrated, interposed therebetween. The substrate solution pipetting unit 26 pipettes, into each reaction vessel 3a that has been subjected to the secondary BF separation, a substrate solution containing a chemiluminescent substrate that specifically reacts with a labeling reagent (enzyme antibody) in an immune complex in which the labeling reagent is bounded with a magnetic reagent and an intended substance such as an antigen. Each reaction vessel 3a holding the substrate solution is transported to a predetermined position by a rotation of the immuno-enzyme reaction unit 10. The reaction vessel 3a that has been transported to the predetermined position is shifted to the luminescence measurement unit 16 by the vessel transfer arm 15.

The luminescence measurement unit 16 is a photometer portion that includes a photomultiplier (PMT) 16a for use as a detector. The luminescence measurement unit 16 measures, using photon counting, light emission phenomena caused by an immune complex and a chemiluminescent substrate. Specifically, the luminescence measurement unit 16 measures the amount of light emitted. A light measurement signal corresponding to a light beam (amount of light emitted) detected by the luminescence measurement unit 16 is digitized by an analog-digital converter, not illustrated. The digitized light measurement signal is then input to the controlling device 60 through components such as a serial interface and is then subjected to an analysis.

Each unit of the above-described measuring device 2 operates in accordance with a command from the controlling device 60.

[Control System of Automatic Analysis Device]

Figure 3:
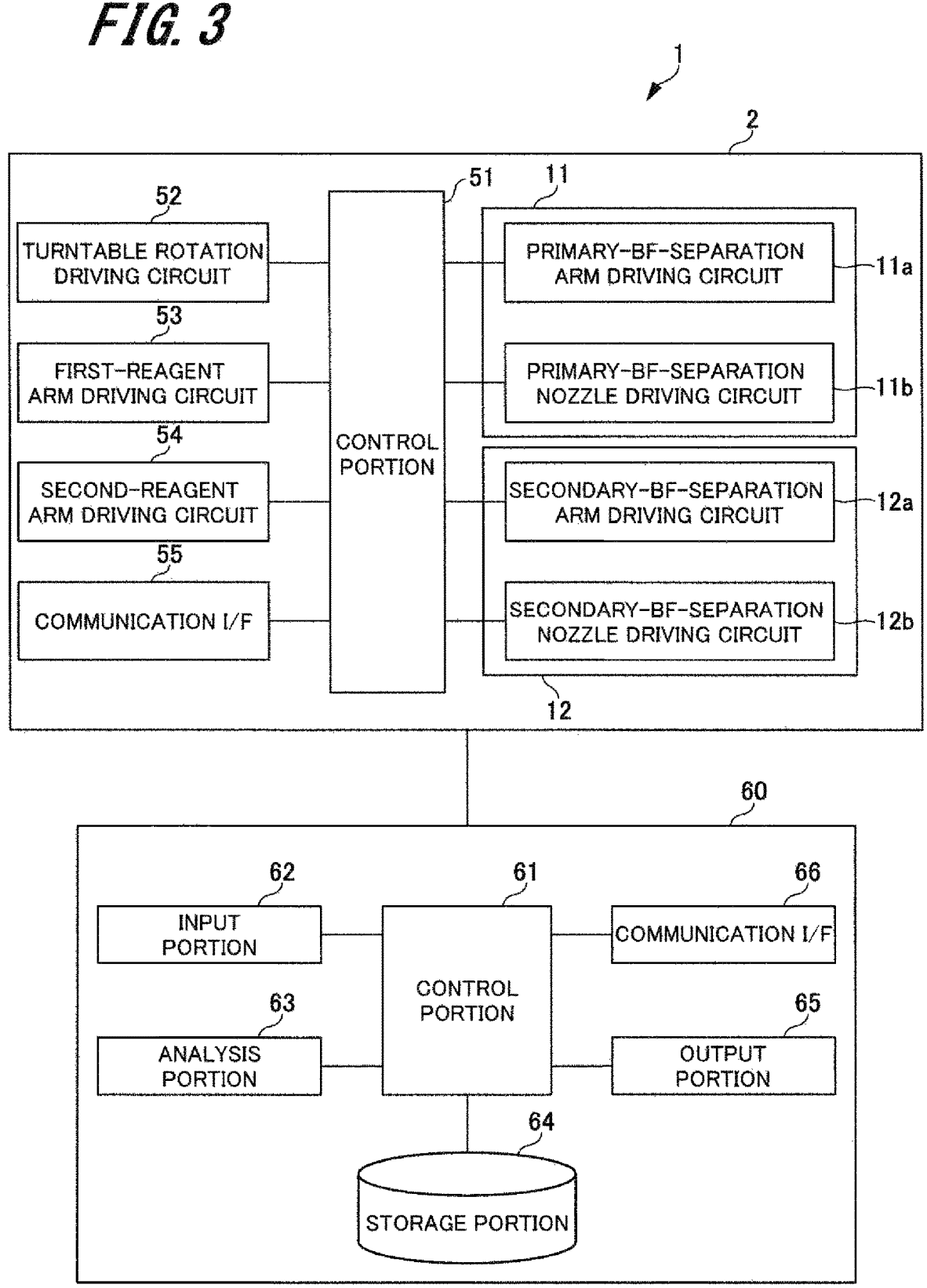
FIG. 3 is a configuration diagram of a control system of the automatic analysis device illustrated in FIG. 1.

Referring now to FIG. 3, a control system of the automatic analysis device 1 is described. FIG. 3 illustrates a configuration of the control system of the automatic analysis device 1, particularly, a portion for controlling the separation step in an immune analysis.

As illustrated in FIG. 3, the measuring device 2 of the automatic analysis device 1 includes a control portion 51, a turntable rotation driving circuit 52, a first-reagent arm driving circuit 53, a second-reagent arm driving circuit 54, and a communication interface 55 (expressed as "communication I/F" in FIG. 3). The measuring device 2 also includes a primary-BF-separation arm driving circuit 11a and a primary-BF-separation nozzle driving circuit 11b of the first BF separation unit 11 and a secondary-BF-separation arm driving circuit 12a and a secondary-BF-separation nozzle driving circuit 12b of the second BF separation unit 12.

The control portion 51 includes, for example, a central processing unit (CPU), a read only memory (ROM), not illustrated, which stores a program, and a random access memory (RAM), used as a working area of the CPU. The control portion 51 is electrically connected to each driving circuit and the communication interface 55 with a system bus, not illustrated, interposed therebetween. The CPU of the control portion 51 is controlled by a control portion 61 of the controlling device 60 to control the process or the operation of each component in the measuring device 2.

The turntable rotation driving circuit 52 generates, on the basis of a control signal fed from the control portion 51, a driving signal for rotating the reagent cooling unit 7 and the immuno-enzyme reaction unit 10 and feeds the driving signal to a driving mechanism, not illustrated. The first-reagent arm driving circuit 53 and the second-reagent arm driving circuit 54 each generate, on the basis of a control signal fed from the control portion 51, a driving signal for driving the arm and the probe of the corresponding one of the first reagent pipetting unit 8 and the second reagent pipetting unit 9 and feed the driving signal to a driving mechanism, not illustrated.

The primary-BF-separation arm driving circuit 11a and the primary-BF-separation nozzle driving circuit 11b of the first BF separation unit 11 each generate, on the basis of a control signal fed from the control portion 51, a driving signal for driving the corresponding one of the arm 25 and the nozzle 21 of the first BF separation unit 11 and feed the driving signal to a driving mechanism, not illustrated. The secondary-BF-separation arm driving circuit 12a and the secondary-BF-separation nozzle driving circuit 12b of the second BF separation unit 12 each generate, on the basis of a control signal fed from the control portion 51, a driving signal for driving the corresponding one of the arm 25 and the nozzle 21 of the second BF separation unit 12 and feed the driving signal to a driving mechanism, not illustrated.

The communication interface 55 is an interface that transmits and receives information in a predetermined form between itself and the controlling device 60 with a communication network, not illustrated, interposed therebetween. An example used as the communication interface 55 is a serial interface.

As illustrated in FIG. 3, the controlling device 60 includes the control portion 61, an input portion 62, an analysis portion 63, a storage portion 64, an output portion 65, and a communication interface (expressed as "communication I/F" in FIG. 3) 66.

The control portion 61 includes, for example, a CPU, a ROM, not illustrated, which stores a program, and a RAM, used as a working area of the CPU. The CPU of the control portion 61 retrieves the program stored in the ROM to the RAM and controls the process and the operation of each component of the automatic analysis device 1 in accordance with this program. The control portion 61 is electrically connected to the input portion 62, the analysis portion 63, the storage portion 64, the output portion 65, and a communication interface 66 with a system bus, not illustrated, interposed therebetween. The controlling device 60 controls a reaction step, a separation step (BF separation), and a light measurement step in an immune analysis using various programs related to the processes of the automatic analysis device 1.

The input portion 62 is a portion through which measurement categories and the like are input to the control portion 61. Examples used as the input portion 62 include a keyboard and a mouse.

The analysis portion 63 is connected to the luminescence measurement unit 16 with the control portion 61 interposed therebetween. The analysis portion 63 analyzes, for example, a component density among the measurement categories of the sample on the basis of the amount of light received by the luminescence measurement unit 16 and outputs the analysis result to the control portion 61.

The storage portion 64 is a nonvolatile mass storage device. The storage portion 64 stores various types of information including, for example, measurement conditions for each measurement category of the sample or analysis results of each measurement category of the sample. Examples used as the storage portion 64 include a storage device such as a solid state drive (SSD) or a magnetism disk. The storage portion 64 may include an auxiliary storage device capable of retrieving information stored in a storage medium such as an optical disk, a magneto-optical disk, an IC card, or a SD card.

The output portion 65 includes, for example, a display (display portion), a speaker, and a printer. The output portion 65 outputs various types of information related to an analysis of the sample under the control of the control portion 61. The display displays the contents of or warnings about an analysis of the sample. The input portion 62 and the display portion may be embodied by a touch screen.

The communication interface 66 is an interface that transmits and receives information in a predetermined form between itself and the measuring device 2 with a communication network, not illustrated, interposed therebetween. An example used as the communication interface 66 is a serial interface.

The control portion 61 outputs a command on each driving circuit of the measuring device 2 through the communication interface 66 to control the separation step in the immune analysis. The measuring device 2 and the controlling device 60 communicate with each other through the communication interface 55 and the communication interface 66. In the following description, however, communications between the measuring device 2 and the controlling device 60 are described without the intervention of the communication interfaces 55 and 66.

[BF Separation Step]

Now, the flow of the BF separation step performed by the first BF separation unit 11 and the second BF separation unit 12 of the measuring device 2 is described.

Figure 4:
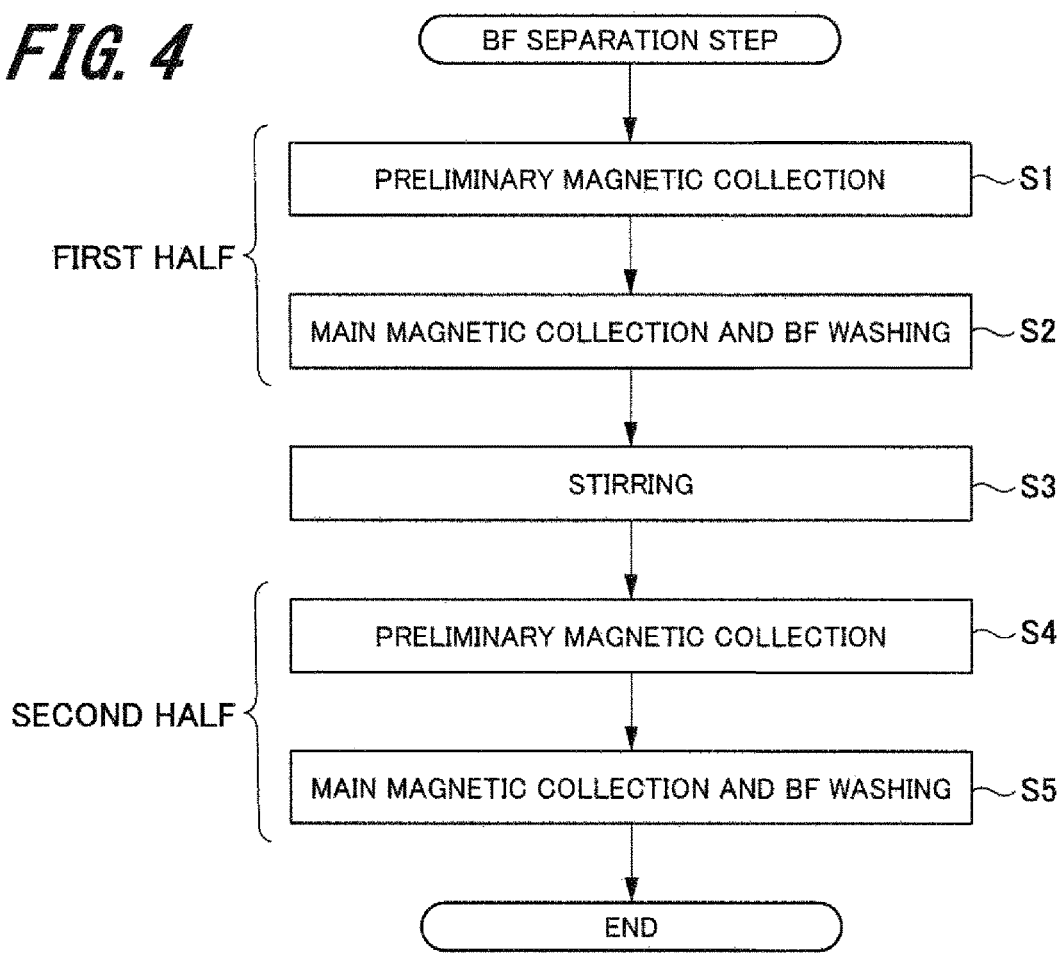
FIG. 4 is a flowchart showing a BF separation step.

FIG. 4 is a flowchart of the BF separation step performed by the first BF separation unit 11 and the second BF separation unit 12 of the measuring device 2.

The basic flow of the BF separation step performed by the first BF separation unit 11 and that performed by the second BF separation unit 12 are the same, so that the flow of the BF separation step (primary BF separation) performed by the first BF separation unit 11 is described here.

In the BF separation step, the first magnetic generation part 32p of the first-half magnetic collection mechanism 31 firstly performs preliminary magnetic collection (step S1) on a reaction vessel 3a that has been transported thereto in a first half of the primary BF separation. Thus, the magnetic particles contained in the liquid sample held in the reaction vessel 3*a* are roughly magnetically collected at (attracted to) the inner wall surface of the reaction vessel 3*a*.

Subsequently, the second magnetic generation part 32*m* of the first-half magnetic collection mechanism 31 performs main magnetic collection and BF washing to magnetically collect the magnetic particles roughly magnetically collected during the preliminary magnetic collection and to hold the magnetic particles on the inner wall surface of the reaction vessel 3*a* (step S2). This main magnetic collection allows a lump of the magnetic particles magnetically collected on the inner wall surface of the reaction vessel 3*a* during the preliminary magnetic collection to be magnetically collected (sucked) to a further localized portion of the inner wall surface of the reaction vessel 3*a*.

Thereafter, the sample in the reaction vessel 3*a* is stirred by the stirring system 39-1 (step S3). This stirring disperses magnetic particles or components not containing the magnetic particles confined in the lump of the magnetic particles magnetically collected on the inner wall surface of the reaction vessel 3*a* by the first-half magnetic collection mechanism 31.

Subsequently, the first magnetic generation part 34*p* of the second-half magnetic collection mechanism 33 performs preliminary magnetic collection (step S4) in a second half of the primary BF separation on a reaction vessel 3*a* that has been transported thereto. Thus, the magnetic particles contained in the liquid sample in the reaction vessel 3*a* are roughly magnetically collected (sucked) again on the inner wall surface of the reaction vessel 3*a*.

Subsequently, the second magnetic generation part 34*m* of the second-half magnetic collection mechanism 33 performs main magnetic collection and BF washing to magnetically collect the magnetic particles roughly magnetically collected again during the preliminary magnetic collection and to hold the magnetic particles on the inner wall surface of the reaction vessel 3*a* (step S5). This main magnetic collection allows a lump of the magnetic particles magnetically collected on the inner wall surface of the reaction vessel 3*a* during the preliminary magnetic collection to be magnetically collected (sucked) to a further localized portion of the inner wall surface of the reaction vessel 3*a*. When the BF washing is complete, the BF separation step is finished.

Similarly, in the second BF separation unit 12, the first-half magnetic collection mechanism 35 and the second-half magnetic collection mechanism 37 perform the steps illustrated in FIG. 4.

Figure 5:
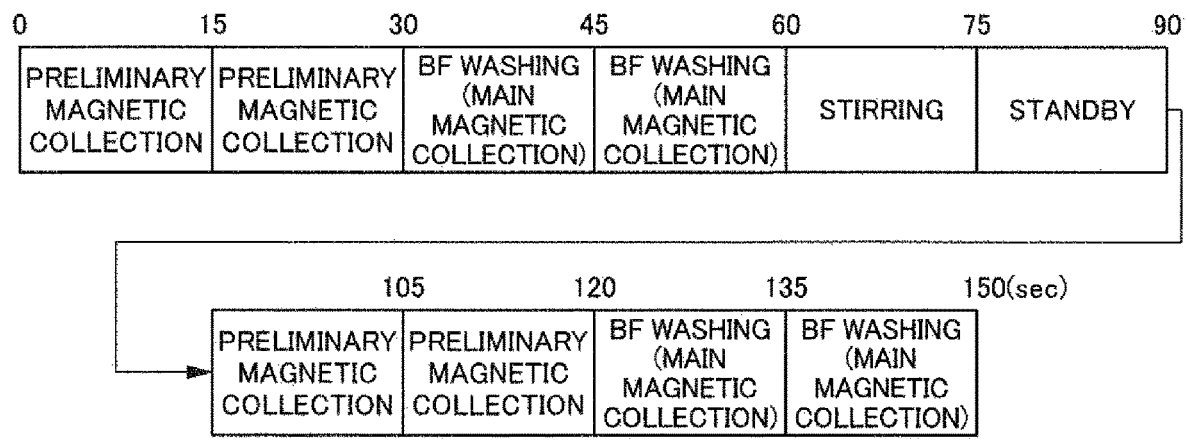
FIG. 5 is a timing chart of the BF separation step.

The automatic analysis device 1 operates in a cycle of, for example, 15 seconds. The turntable of the immuno-enzyme reaction unit 10 rotates in a 15-second cycle. FIG. 5 illustrates a timing chart of the BF separation step performed on one reaction vessel 3*a*. When the automatic analysis device 1 operates in a 15-second cycle and performs magnetic collection on two reaction vessels 3*a* at a time, the reaction vessels 3*a* are transported to the magnetic collection position, two cycles of a first half of the preliminary magnetic collection are then performed, and two cycles of BF washing (main magnetic collection) are then performed. Thereafter, one cycle of stirring is performed on the reaction vessels 3*a* and the reaction vessels 3*a* are left on standby for a period corresponding to one cycle. Thereafter, two cycles of a second half of the preliminary magnetic collection are performed and then two cycles of BF washing (main magnetic collection) are performed. The time length required from the start of the first half of the preliminary magnetic collection to the completion of the second half of the BF washing (main magnetic collection) is 150 sec.

The invention is not limited to the embodiment in which each process is performed per two cycles. Each process may be performed by one cycle at a time as long as a sufficiently large magnetic collection effect can be obtained through the cycle or each process may be performed by three cycles or more at a time if the effect is not sufficient. Embodiments of a first-half magnetic collection mechanism (first magnetic generation part and second magnetic generation part) and a second-half magnetic collection mechanism (first magnetic generation part and second magnetic generation part) used for performing a process by one cycle and three cycles at a time are described below.

Thereafter, the positional relationship during the BF separation step between the reaction vessels 3*a* and the first and second magnetic generation parts 32*p*, 32*m*, 34*p*, and 34*m* (see FIG. 1 and FIG. 2) is described.

Figure 6:
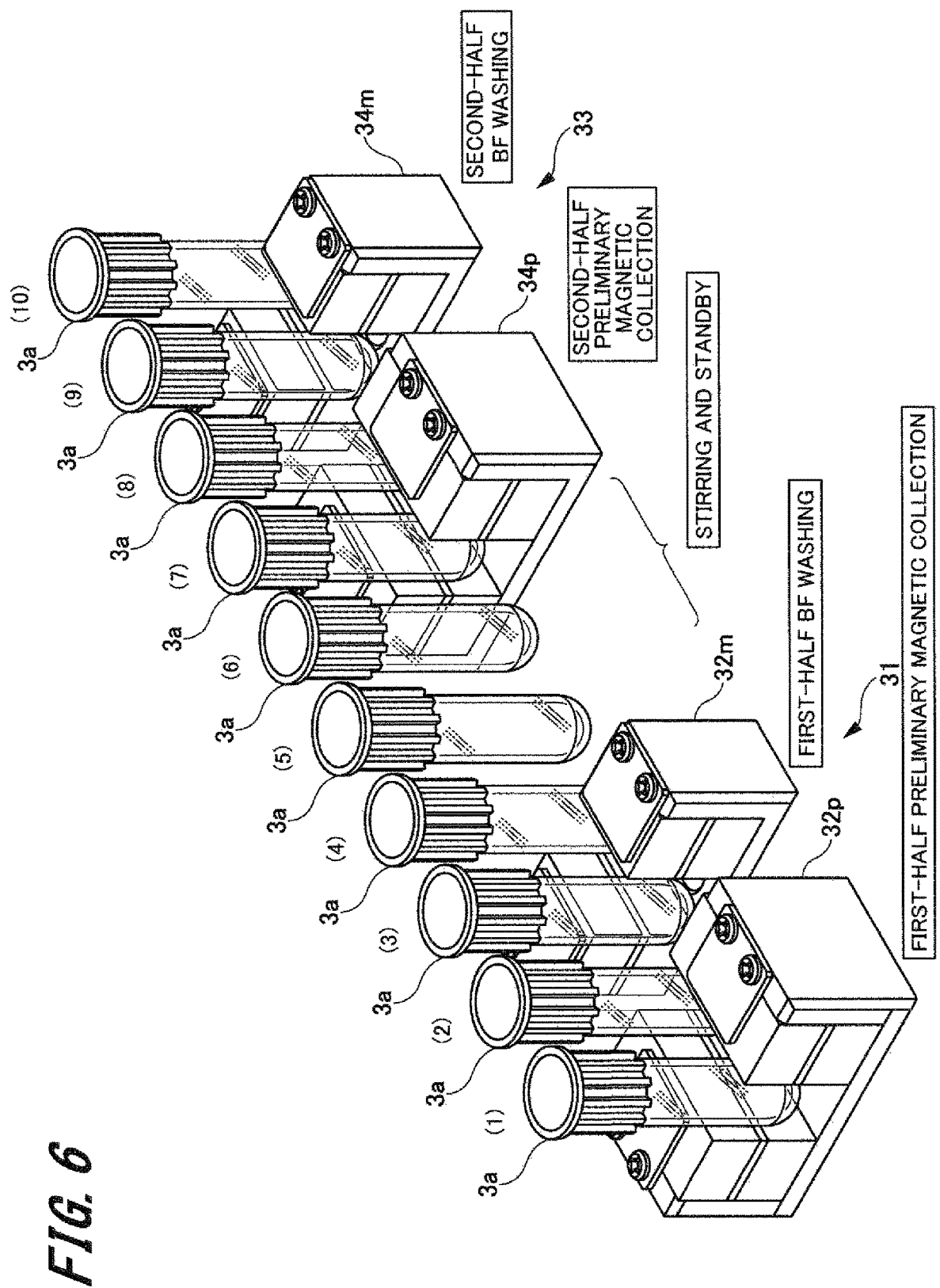
FIG. 6 illustrates, in a schematic perspective view, the positional relationship between reaction vessels and magnetic generation parts during the BF separation step.

FIG. 6 illustrates, in a schematic perspective view, the positional relationship during the BF separation step between the reaction vessels 3*a* and the first and second magnetic generation parts 32*p*, 32*m*, 34*p*, and 34*m*.

FIG. 7 illustrates, in a schematic diagram, the positional relationship during the BF separation step between the reaction vessels 3*a* and the first and second magnetic generation parts 32*p*, 32*m*, 34*p*, and 34*m*, where an upper part of FIG. 7 is a top view and a lower part of FIG. 7 is a sectional view taken along line A-A. For the simplicity of illustration, however, the upper part of FIG. 7 excludes an illustration of the lower layer 10*b* of the turntable and the lower part of FIG. 7 excludes an illustration of sections of the reaction vessels 3*a*.

FIG. 6 and FIG. 7 clearly illustrate the positional relationship during the BF separation step between the reaction vessels 3*a* and the first and second magnetic generation parts 32*p*, 32*m*, 34*p*, and 34*m* while the first and second magnetic generation parts 32*p*, 32*m*, 34*p*, and 34*m* arranged in the circumferential direction are illustrated as being arranged linearly along the BF separation step. One BF separation step (primary BF separation) flows from the near side on the left to the far side on the right in FIG. 6 and from the left to the right in FIG. 7. The positional relationship between the reaction vessels 3*a* and the first and second magnetic generation parts 36*p*, 36*m*, 38*p*, and 38*m* remains the same also in the secondary BF separation. The two-directional arrow Dc denotes an effective diameter (inner diameter) of a body portion of each reaction vessel 3*a*.

The numbers of the positions of the reaction vessels 3*a* illustrated in FIG. 6 and FIG. 7 represent the following positions:

positions (1) and (2) denote first-half preliminary magnetic collection positions;

positions (3) and (4) denote first-half BF washing positions (main magnetic collection positions);

position (5) denotes a stirring position;

position (6) denotes a standby position;

positions (7) and (8) denote second-half preliminary magnetic collection positions; and positions (9) and (10) denote second-half BF washing positions (main magnetic collection positions).

Figure 8:
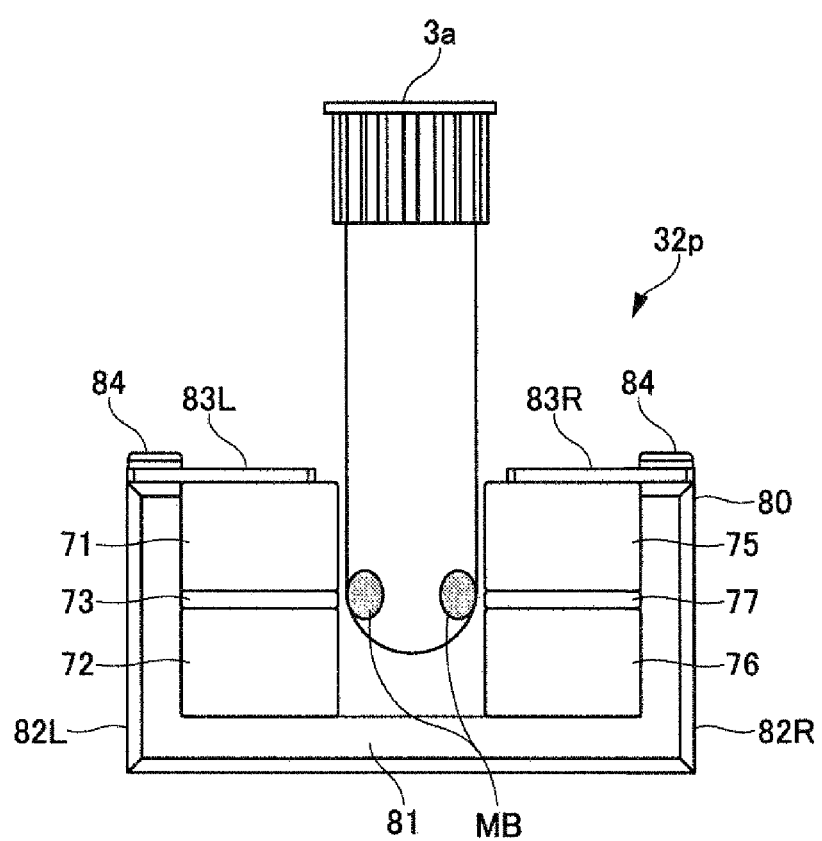
FIG. 8 illustrates, in a side view, the positional relationship between a reaction vessel and a magnetic generation part.

FIG. 8 is a side view of the positional relationship between a reaction vessel 3*a* and a magnetic generation part. FIG. 8 illustrates the first magnetic generation part 32*p* as an example of the magnetic generation part.

In areas MB in the reaction vessel 3*a* illustrated in FIG. 8 or the vicinity of the areas MB, magnetic particles contained in the liquid sample in the reaction vessel 3*a* are attracted to the inner wall surface of the reaction vessel 3*a* by the effect of magnets 71, 72, 75, and 76 of the first magnetic generation part 32p. The reason why the magnetic particles are magnetically collected at two separate points is because the magnetic fields are produced on the left and right side of each reaction vessel 3a that has been transported to the first magnetic generation part 32p. The detailed configuration of each magnetic generation part and the detailed positional relationship between each reaction vessel 3a and the corresponding magnetic generation part are separately described below.

[Structure of Magnetic Generation Part for Preliminary Magnetic Collection]

Figure 9:
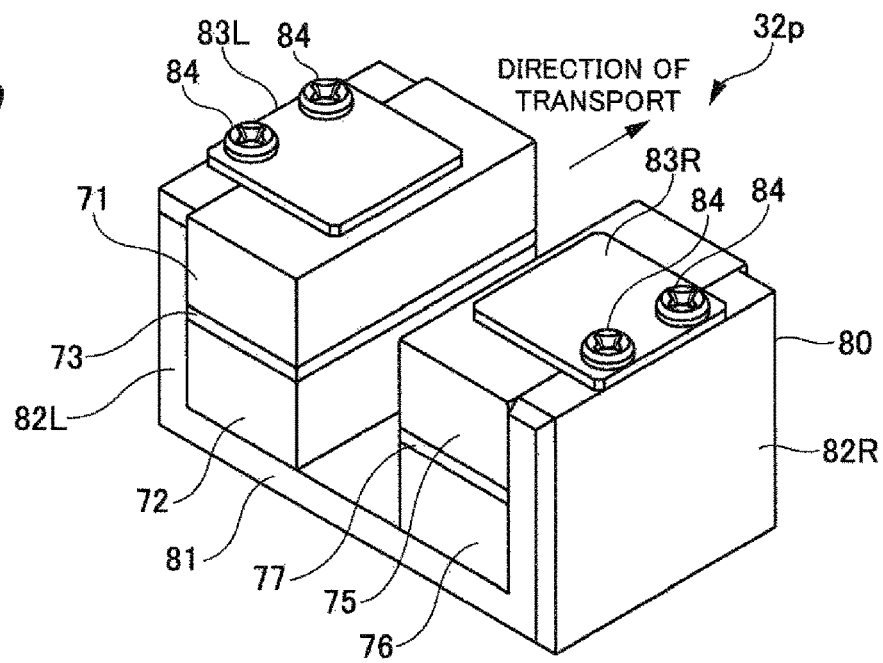
FIG. 9 is a perspective view of a first magnetic generation part used for preliminary magnetic collection.
Figure 11:
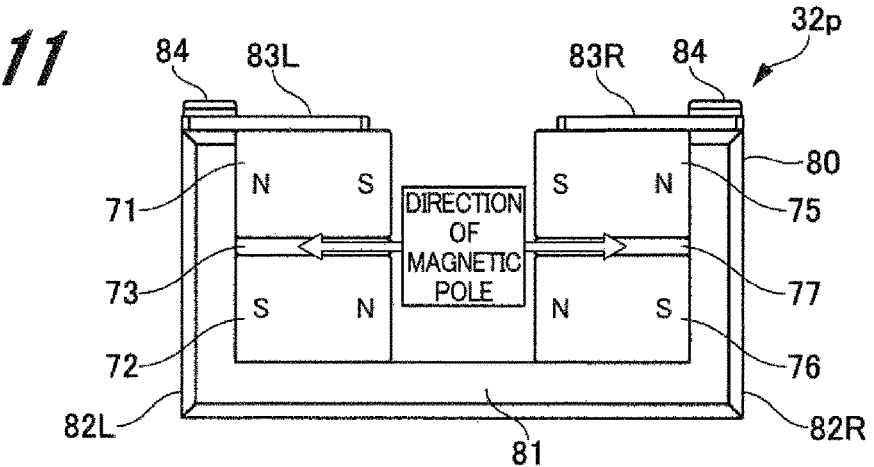
FIG. 11 is a side view of the first magnetic generation part illustrated in FIG. 9.

Referring now to FIG. 9 and FIG. 11, the structure of each of the first magnetic generation parts 32p, 34p, 36p, and 38p used for preliminary magnetic collection is described in detail. The first magnetic generation parts 32p, 34p, 36p, and 38p, however, have the same structure and thus, only the first magnetic generation part 32p is described below.

FIG. 9 is a perspective view of the first magnetic generation part 32p used for preliminary magnetic collection.

Figure 10:
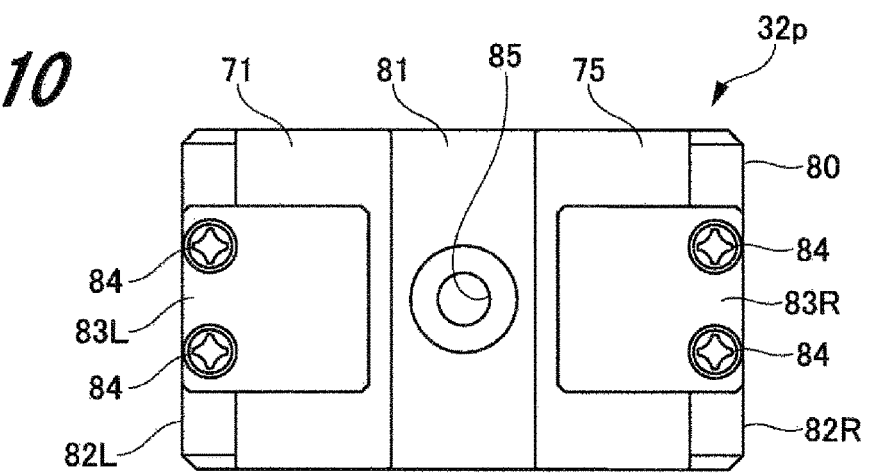
FIG. 10 is a top view of the first magnetic generation part illustrated in FIG. 9.

FIG. 10 is a top view of the first magnetic generation part 32p.

FIG. 11 is a side view of the first magnetic generation part 32p.

The first magnetic generation part 32p includes four magnets 71, 72, 75, and 76 having the same rectangular parallelepiped shape (see FIG. 9). The magnet 71 (first magnet) and the magnet 72 (second magnet) are arranged vertically so that different magnetic poles face each other. Specifically, each of the magnet 71 and the magnet 72 has a first magnetic pole (for example, north pole) and a second magnetic pole (for example, south pole) arranged in a direction that is horizontal and that is perpendicular to the vessel transport direction (see FIG. 11). An arrangement of the magnetic poles of the magnet 71 in a direction that is horizontal and that is perpendicular to the vessel transport direction is opposite to an arrangement of the magnetic poles of the magnet 72 in the direction that is horizontal and that is perpendicular to the vessel transport direction, that is, the magnetic poles of opposing surfaces of the magnet 71 and the magnet 72 are opposite to each other. A nonmagnetic member 73 (such as aluminium sheet) is disposed between the magnet 71 and the magnet 72.

Similarly to the magnet 71 and the magnet 72, the magnet 75 (third magnet) and the magnet 76 (fourth magnet) are also arranged vertically so that different magnetic poles face each other. A nonmagnetic member 77 (such as aluminium sheet) is disposed between the magnet 75 and the magnet 76. The pair of magnets 71 and 72 and the pair of magnets 75 and 76 are disposed so as to face each other across the path (groove 49d). The opposing surfaces of the magnet 71 and the magnet 75 have a south pole and the opposing surfaces of the magnet 72 and the magnet 76 have a north pole (see FIG. 11). The first magnetic generation part 32p includes a set of these four magnets 71, 72, 75, and 76.

Examples used as the four magnets 71, 72, 75, and 76 for preliminary magnetic collection are permanent magnets according to, for example, Japan Industrial Standard (JIS C 2502). Japan Industrial Standard classifies permanent magnets into three types, that is, hard magnetic alloys, hard magnetic ceramics, and bonded magnets. Examples well known as a permanent magnet include a permanent magnet containing a rare earth exemplified by, for example, neodymium.

The magnets 71, 72, 75, and 76 are fixed to a yoke 80 made of a ferromagnetic substance (such as an iron material). The yoke 80 has a letter U shape. The yoke 80 has a bottom board portion 81, with which the lower surfaces of the magnets 72 and 76 come into contact. The yoke 80 also has a left wall 82L, with which side surfaces of the magnets 71 and 72 come into contact, and a right wall 82R, with which side surfaces of the magnets 75 and 76 come into contact. Male screws 84 are screwed in female screws formed at upper end portions of the left wall 82L, so that a fastening plate 83L is pressed against the upper surface of the magnet 71. Similarly, male screws 84 are screwed in female screws formed at upper end portions of the right wall 82R, so that a fastening plate 83R is pressed against the upper surface of the magnet 75. Attaching the magnets 71, 72, 75, and 76 to the yoke 80 can form a magnetic circuit and prevent a leakage of the magnetic field to the outside. In addition, the first magnetic generation part 32p including the four magnets 71, 72, 75, and 76 can be easily fixed to the lower layer 10b of the turntable.

Figure 12A:
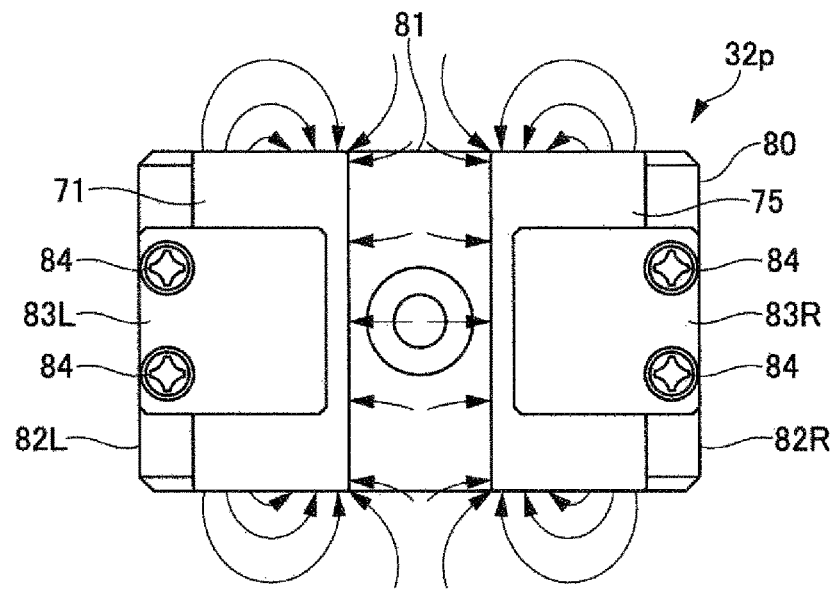
FIGS. 12A and 12B are schematic diagrams of lines of the magnetic force exerted by the first magnetic generation part, where
Figure 12B:
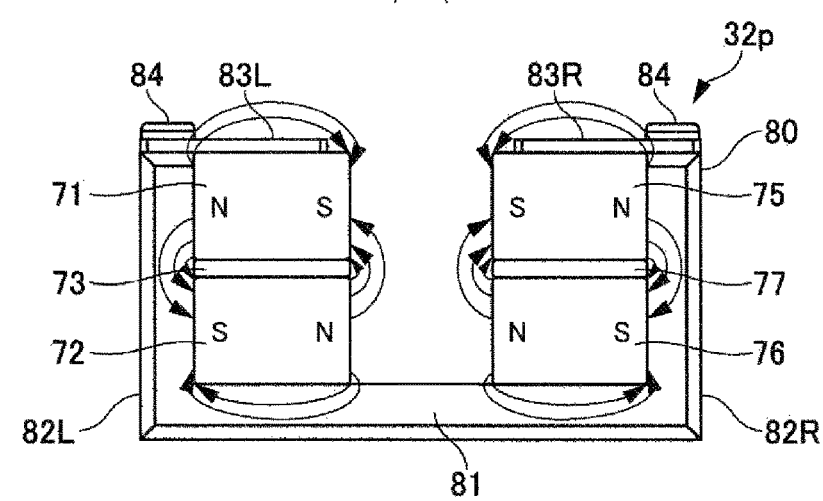

FIGS. 12A and 12B are schematic diagrams of lines of the magnetic force output by the first magnetic generation part 32p, where FIG. 12A illustrates lines of the magnetic force viewed from above the first magnetic generation part 32p and FIG. 12B illustrates lines of the magnetic force viewed from the side of the first magnetic generation part 32p.

The first magnetic generation part 32p having the above-described configuration forms a closed magnetic circuit using the magnets 71 and 72 and the yoke 80, as illustrated in FIG. 12B. The first magnetic generation part 32p also forms a closed magnetic circuit using the magnets 75 and 76 and the yoke 80. It is known that magnets have high magnetic collection ability at their corners. In the example illustrated in FIG. 12A, lines of the magnetic force are crowded and the magnetic flux density is high at both end portions (corner portions) of the surface of the magnet 71 (72) facing the magnet 75 (76). In the example illustrated in FIG. 12B, lines of the magnetic force are crowded and the magnetic flux density is high at both end portions (corner portions) of the surfaces of the magnet 71 and the magnet 72 facing each other. Similarly, lines of the magnetic force are crowded and the magnetic flux density is high at both end portions (corner portions) of the surfaces of the magnet 75 and the magnet 76 facing each other.

Figure 13:
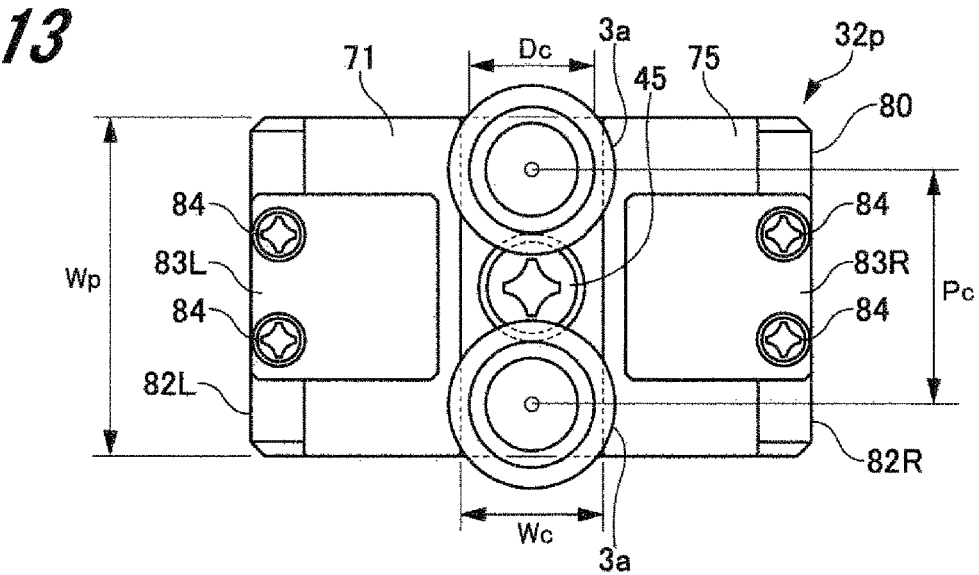
FIG. 13 illustrates the positional relationship between the reaction vessels and the first magnetic generation part.

FIG. 13 illustrates the positional relationship between the reaction vessels 3a and the first magnetic generation part 32p.

The surface of each magnet of the first magnetic generation part 32p used for preliminary magnetic collection facing the reaction vessels 3a has a width Wp in the vessel transport direction that is as long as to cover effective areas of two reaction vessels 3a transported to the magnetic collection position of the first magnetic generation part 32p and spaced a predetermined arrangement pitch (distance) apart from each other. Here, each effective area is an area (space) that holds, for example, the sample in the body portion of the reaction vessel 3a. The dimension of the area in the vessel transport direction, that is, the inner diameter of the body portion is referred to as an effective diameter.

When the effective diameter (inner diameter) of the body portion of each reaction vessel 3a is denoted with Dc and the arrangement pitch at which the reaction vessels 3a are arranged (arranged in the circumferential direction in an actual immuno-enzyme reaction unit 10) is denoted with Pc, the width Wp of the first magnetic generation part 32p can be determined using the following formula:

$$Wp \geq Dc + Pc \qquad (1).$$

In the preliminary magnetic collection, disposing each reaction vessel 3a at a portion located inward from both end portions of the magnet 71 (72, 75, or 76) is important. To this end, the magnet 71 (72, 75, or 76) having a large width Wp is suitable. In other words, preferably, the effective area of each reaction vessel 3a is located within an area interposed between two imaginary lines, which are straight lines imaginarily drawn from both ends of the magnet 71 (72, 75, or 76) so as to be perpendicular to the vessel transport direction. A gap We between the opposing magnets 71 (72) and 75 (76) is determined to be a minimum possible distance that does not hinder the reaction vessels 3a to pass therethrough.

The positional relationship between each reaction vessel 3a and the magnet 71 (72, 75, or 76) that satisfies the formula (1) is not suitable for collecting the magnetic particles in the liquid sample inside the reaction vessel 3a at one point. In this case, however, the magnetic force of the magnet 71 (72, 75, or 76) is exerted on the entirety of the liquid sample inside the reaction vessel 3a. Such a positional relationship is thus effective for roughly collecting the magnetic particles widely dispersed inside the liquid sample at one point.

[Structure of Magnetic Generation Part for Main Magnetic Collection]

Figure 14:
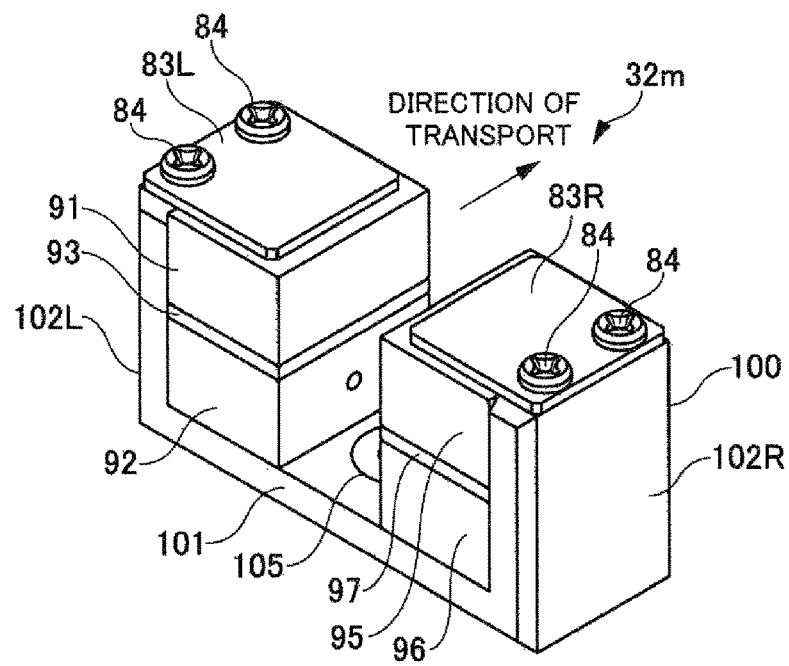
FIG. 14 is a perspective view of a second magnetic generation part used for main magnetic collection.
Figure 15:
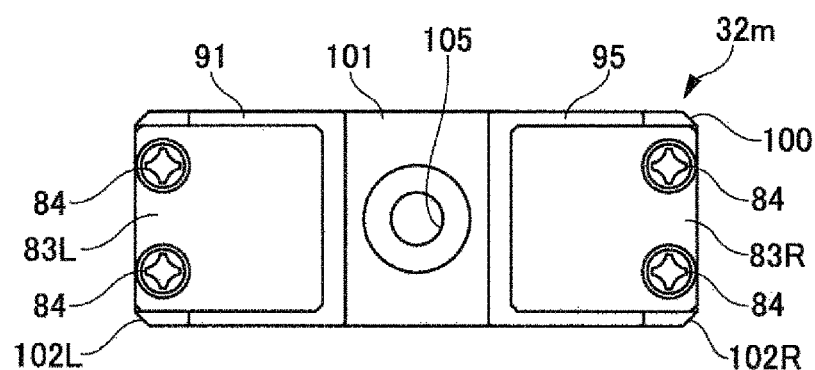
FIG. 15 is a top view of the second magnetic generation part illustrated in FIG. 14.
Figure 16:
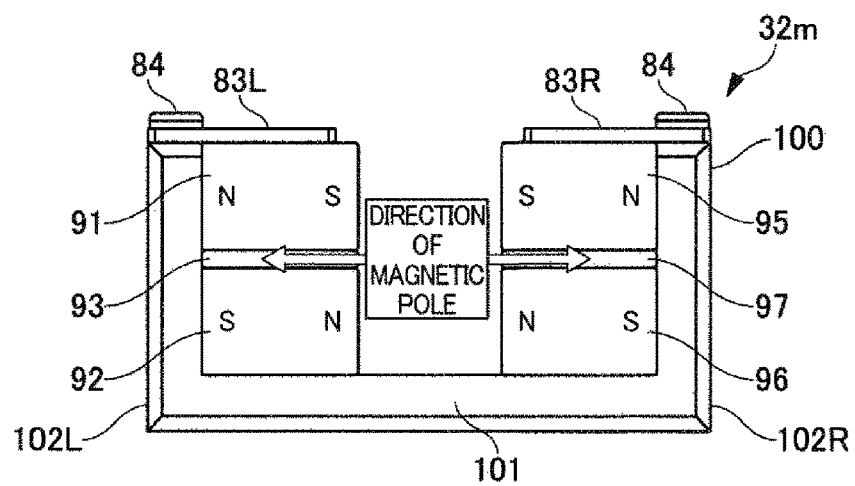
FIG. 16 is a side view of the second magnetic generation part illustrated in FIG. 14.

Referring now to FIG. 14 to FIG. 16, the structure of the second magnetic generation parts 32m, 34m, 36m, and 38m used for main magnetic collection is described in detail. Since the second magnetic generation parts 32m, 34m, 36m, and 38m, however, have the same structure, only the structure of the second magnetic generation part 32m is described below.

FIG. 14 is a perspective view of the second magnetic generation part 32m used for the main magnetic collection.

FIG. 15 is a top view of the second magnetic generation part 32m.

FIG. 16 is a side view of the second magnetic generation part 32m.

The basic structure of the second magnetic generation part 32m is the same as that of the first magnetic generation part 32p for preliminary magnetic collection. However, the way how the width Wm of the second magnetic generation part 32m in the vessel transport direction is determined is significantly different from that in the case of the first magnetic generation part 32p.

The second magnetic generation part 32m includes four magnets 91, 92, 95, and 96 having the same rectangular parallelepiped shape (see FIG. 14). The magnets 91, 92, 95, and 96 are assembled in the same manner as are the magnets 71, 72, 75, and 76 of the first magnetic generation part 32p (34p, 36p, or 38p). Here, the width of the magnets 91, 92, 95, and 96 in the vessel transport direction is shorter than the width of the magnets 71, 72, 75, and 76 of the first magnetic generation part 32p (34p, 36p, or 38p). The magnet 91 (first magnet) and the magnet 92 (second magnet) are arranged vertically so that different magnetic poles face each other. Specifically, each the magnet 91 and the magnet 92 has a first magnetic pole (for example, north pole) and a second magnetic pole (for example, south pole) arranged in a direction that is horizontal and that is perpendicular to the vessel transport direction and the magnet 91 and the magnet 92 are disposed so that their opposing magnetic poles are opposite to each other (see FIG. 16). A nonmagnetic member 93 (such as aluminium sheet) is disposed between the magnet 91 and the magnet 92.

Similarly to the magnet 91 and the magnet 92, the magnet 95 (third magnet) and the magnet 96 (fourth magnet) are also arranged vertically so that different magnetic poles face each other. A nonmagnetic member 97 (such as aluminium sheet) is disposed between the magnet 95 and the magnet 96. The pair of magnets 91 and 92 and the pair of magnets 95 and 96 are disposed so as to face each other across the path (groove 49d). The opposing surfaces of the magnet 91 and the magnet 95 have a south pole and the opposing surfaces of the magnet 92 and the magnet 96 have a north pole (see FIG. 16). The second magnetic generation part 32m includes a set of these four magnets 91, 92, 95, and 96.

Examples used as the four magnets 91, 92, 95, and 96 for main magnetic collection include permanent magnets, as in the case of the magnets 71, 72, 75, and 76 for preliminary magnetic collection.

The magnets 91, 92, 95, and 96 are fixed to a yoke 100, made of a ferromagnetic substance (such as an iron material). The width of the yoke 100 in the vessel transport direction is smaller than that of the first magnetic generation part 32p so as to correspond to the width of the magnets 91, 92, 95, and 96. The yoke 100 has a letter U shape. The yoke 100 has a bottom board portion 101, with which the lower surfaces of the magnets 92 and 96 come into contact. The yoke 100 also has a left wall 102L, with which the side surfaces of the magnets 91 and 92 come into contact, and a right wall 102R, with which the side surfaces of the magnets 95 and 96 come into contact. Male screws 84 are screwed in female screws formed at upper end portions of the left wall 102L, so that a fastening plate 83L is pressed against the upper surface of the magnet 91. Similarly, male screws 84 are screwed in female screws formed at upper end portions of the right wall 102R, so that a fastening plate 83R is pressed against the upper surface of the magnet 95.

The second magnetic generation part 32m having this configuration forms substantially the same magnetic fields as does the first magnetic generation part 32p (see FIG. 12). Specifically, lines of the magnetic force are crowded and the magnetic flux density is high at both end portions (corner portions) of the surface of the magnet 91 (92) facing the magnet 95 (96). In addition, lines of the magnetic force are crowded and the magnetic flux density is high at both end portions (corner portions) of the surfaces of the magnet 91 and the magnet 92 facing each other. Similarly, lines of the magnetic force are crowded and the magnetic flux density is high at both end portions (corner portions) of the surfaces of the magnet 95 and the magnet 96 facing each other.

Figures 17, 18, 19:
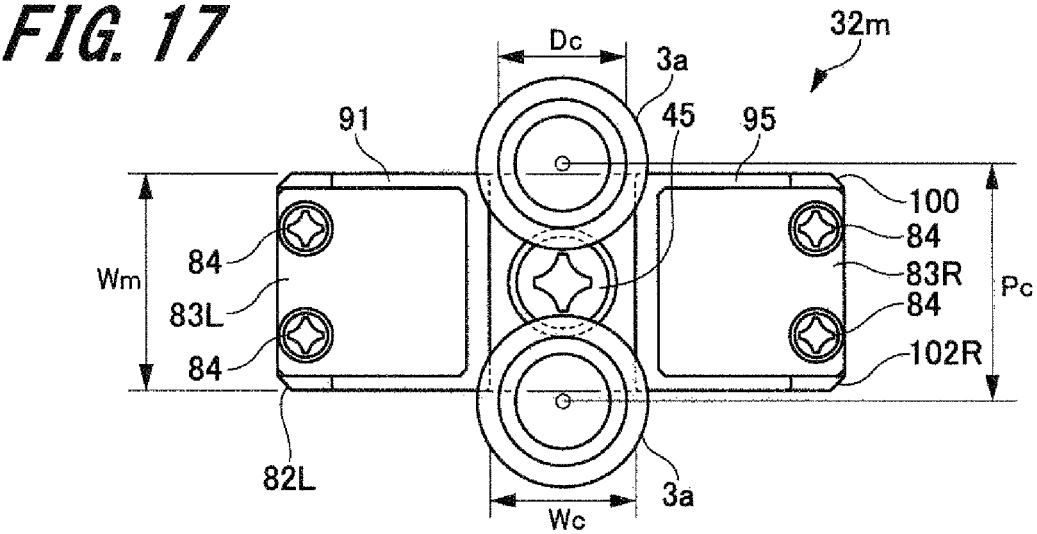
FIG. 17 illustrates the positional relationship between reaction vessels and the second magnetic generation part.
FIG. 18 illustrates an example of measurement data showing the ratio of how many magnetic particles remain in the reaction vessel after a typical BF separation step is performed.
FIG. 19 illustrates an example of measurement data showing the ratio of how many magnetic particles remain in the reaction vessel after a BF separation step according to a first embodiment is performed.

FIG. 17 illustrates the positional relationship between the reaction vessels 3a and the second magnetic generation part 32m (34m, 36m, or 38m).

The surface of each magnet of the second magnetic generation part 32m for main magnetic collection facing the reaction vessels 3a has end portions in the vessel transport direction that are located adjacent to the centers of the inner diameters of the reaction vessels 3a transported to the magnetic collection position of the second magnetic generation part 32m. Specifically, the width Wm of each magnet of the second magnetic generation part 32m in the vessel transport direction is approximately the same as the arrangement pitch (distance) between two reaction vessels 3a that have been transported to the magnetic collection position of the second magnetic generation part 32m.

Here, the width Wm of each magnet of the second magnetic generation part 32m can be determined using the following formula, where the effective diameter (inner diameter) of the body portion of each reaction vessel 3a is denoted with Dc and the arrangement pitch at which the reaction vessels 3a are arranged (arranged in the circumferential direction in an actual immuno-enzyme reaction unit 10) is denoted with Pc:

$$Wm \approx Pc \qquad (2).$$

In the main magnetic collection, it is important to hold the magnetic particles magnetically collected during the preliminary magnetic collection on the inner wall surface of each reaction vessel 3a so that the magnetic particles are not carried away by the flow of the washing liquid. Preferably, approximately center positions of the reaction vessels 3a are roughly aligned with the positions of both end portions of the magnet 91 (92, 95, or 96) in the vessel transport direction. In other words, preferably, the center position of each reaction vessel 3a is located on or substantially on either one of two imaginary lines, which are straight lines imaginarily drawn from both ends of the magnet 91 (92, 95, or 96) in a direction perpendicular to the vessel transport direction.

The positional relationship between the reaction vessels 3a and the magnet 91 (92, 95, or 96) that satisfies the formula (2) is effective in terms that strong magnetic fields produced at both end portions of each magnet 91 (92, 95, or 96) are capable of magnetically locally collecting magnetic particles contained in the liquid sample in the reaction vessels 3a at a point.

[Example of Measurement Data]

FIG. 18 illustrates an example of measurement data of the ratio of how many magnetic particles remain in each reaction vessel 3a after the sample is subjected to a typical BF separation step.

FIG. 19 illustrates an example of measurement data of the ratio of how many magnetic particles remain in each reaction vessel 3a after the sample is subjected to a BF separation step according to the first embodiment.

The BF separation step was performed five times and the ratio (%) of how many magnetic particles remain was measured every time. In FIG. 18 and FIG. 19, "CV" denotes a coefficient of variation.

The ratio (%) of how many magnetic particles remain is an indicator that shows how may magnetic particles originally contained in the liquid sample inside each reaction vessel 3a remain in the reaction vessel 3a after the sample is subjected to the B/F separation step. Before employing this embodiment, the average of the ratios of how many magnetic particles remain measured after five times of the BF separation step is approximately 74% (73.6%) (see FIG. 18). However, the average of the ratios measured after five times of the BF separation step is found to have been improved up to approximately 91% as a result of improving the efficiency of preliminary magnetic collection using this embodiment (see FIG. 19).

[Examples of Magnetically Collected Magnetic Particle Image]

For reference, FIG. 20 illustrates examples of magnetically collected magnetic particle images formed differently depending on magnet shapes.

Figure 20A:
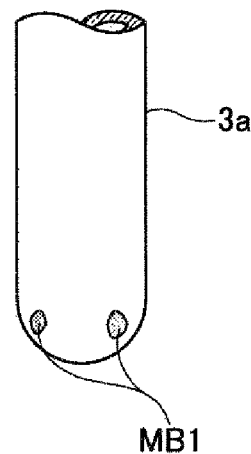
FIGS. 20A, 20B, and 20C illustrate images of magnetically collected magnetic particles remaining in the reaction vessel depending on different magnetic shapes, where

The example illustrated in FIG. 20A is a magnetically collected magnetic particle image MB1 obtained using only the first magnetic generation part 32p. The magnetic particles are magnetically collected to form a lump (dotted form) having a certain size. The diameter of the lump is found to be large.

Figure 20B:
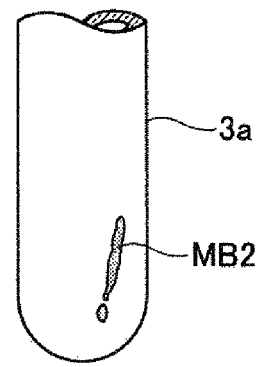

The example illustrated in FIG. 20B is a magnetically collected magnetic particle image MB2 obtained using only the second magnetic generation part 32m. This is a result obtained by imitatively performing an existing method that does not involve preliminary magnetic collection and this method is not directly applicable to this embodiment. Since the second magnetic generation part 32m performs magnetic collection using end portions of the magnets, the magnetic particles are magnetically collected by a strong suction force but fail to form in a dotted form. The image MB2 shows the state where the magnetic particles are magnetically collected linearly extending along the axial direction of the reaction vessel 3a.

Figure 20C:
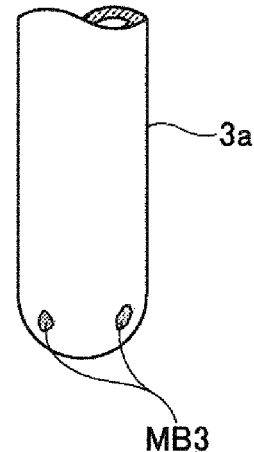

The example illustrated in FIG. 20C is a magnetically collected magnetic particle image MB3 obtained by the first embodiment. Specifically, this is a magnetically collected magnetic particle image obtained after performing preliminary magnetic collection using the first magnetic generation part 32p and then further performing magnetic collection using the second magnetic generation part 32m. Compared with the magnetically collected magnetic particle image MB1 illustrated in FIG. 20A obtained by performing magnetic collection using only the first magnetic generation part 32p, the image MB3 shows the state where the magnetic particles are condensed in smaller dots.

As described above in the first embodiment, the surface of each of the magnets 71, 72, 75, and 76 for preliminary magnetic collection of the first magnetic generation part 32p (34p, 36p, or 38p) facing the reaction vessels 3a has the width Wp in the vessel transport direction that is designed to be as long as to cover the effective areas Dc of the reaction vessels 3a that have been transported to the magnetic collection position of the first magnetic generation part 32p (34p, 36p, or 38p). In addition, the surface of each of the magnets 91, 92, 95, and 96 for main magnetic collection of the second magnetic generation part 32m (34m, 36m, or 38m) facing the reaction vessels 3a has end portions in the vessel transport direction that are designed to be located adjacent to the centers of the effective areas Dc of the reaction vessels 3a that have been transported to the magnetic collection position of the second magnetic generation part 32m (34m, 36m, or 38m).

This configuration allows each of the magnets 71, 72, 75, and 76 of the first magnetic generation part 32p (34p, 36p, or 38p) to exert its magnetic force over the entirety of the liquid sample inside the reaction vessel 3a. Thus, the magnetic particles widely dispersed in the liquid sample are roughly collected at a single point during the preliminary magnetic collection. In addition, the magnetic particles in the liquid sample inside the reaction vessel 3a that have been preliminarily magnetically collected are magnetically and locally collected and held at a point in the main magnetic collection using strong magnetic forces produced at both end portions of each of the magnets 91, 92, 95, and 96 of the second magnetic generation part 32m (34m, 36m, or 38m). This configuration is thus capable of reducing the amount of magnetic particles that are carried away through the washing operation during the BF separation step involving the preliminary magnetic collection and main magnetic collection.

Specifically, this embodiment is capable of improving the preliminary magnetic collection efficiency and improving the suction force exerted during the main magnetic collection as a result of differing the shape of the magnets used for preliminary magnetic collection in the BF separation step from the shape of the magnets used for the main magnetic collection in the BF separation step so that the shapes are appropriate for their purposes. Thus, the automatic analysis device can perform an immune analysis with improved higher detection sensitivity.

<Second Embodiment>

Figure 21:
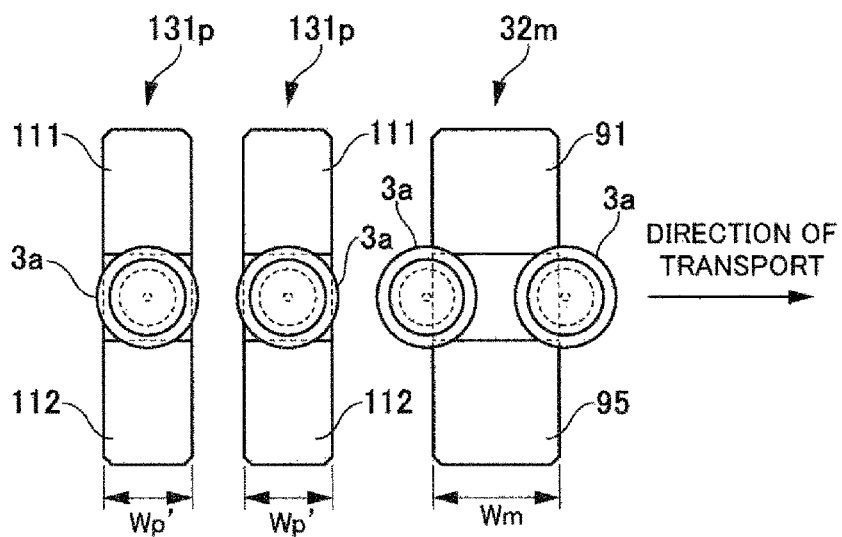
FIG. 21 illustrates first magnetic generation parts and a second magnetic generation part according to a second embodiment of the present invention.

FIG. 21 illustrates a first magnetic generation part and a second magnetic generation part according to a second embodiment of the invention. The first magnetic generation part 32p according to the first embodiment performs preliminary magnetic collection on two reaction vessels 3a at a time. The first magnetic generation part according to the second embodiment, on the other hand, performs preliminary magnetic collection on one reaction vessel 3a at a time. The second magnetic generation part for main magnetic collection has a structure the same as that of the second magnetic generation part 32m according to the first embodiment.

As illustrated in FIG. 21, two first magnetic generation parts 131p for preliminary magnetic collection are arranged in the vessel transport direction. The way how magnets in each first magnetic generation part 131p are assembled together is basically the same as that in the case of the first magnetic generation part 32p. Specifically, the first magnetic generation part 131p includes four magnets, but FIG. 21 illustrates only two magnets 111 and 112 on the upper side. These magnets 111 and 112 correspond to the magnets 71 and 75 of the first magnetic generation part 32p. Similarly to the first magnetic generation part 32p, the first magnetic generation part 131p includes a nonmagnetic member and a yoke (not illustrated).

The surface of each of the magnets 111 and 112 of the first magnetic generation part 131p facing the reaction vessel 3a has a width Wp' in the vessel transport direction that is as long as to cover the effective area (see FIG. 7) of the reaction vessel 3a that has been transported to the magnetic collection position of the first magnetic generation part 131p. Thus, the four magnets of the first magnetic generation part 131p, including the magnets 111 and 112, exert their magnetic forces over the entirety of the liquid sample inside the reaction vessel 3a. The magnetic particles widely dispersed in the liquid sample are thus roughly collected to one point, as in the case of the first embodiment. These two first magnetic generation parts 131p arranged side by side can replace the first magnetic generation part 32p that performs preliminary magnetic collection on two reaction vessels 3a at a time.

<Third Embodiment>

Figure 22:
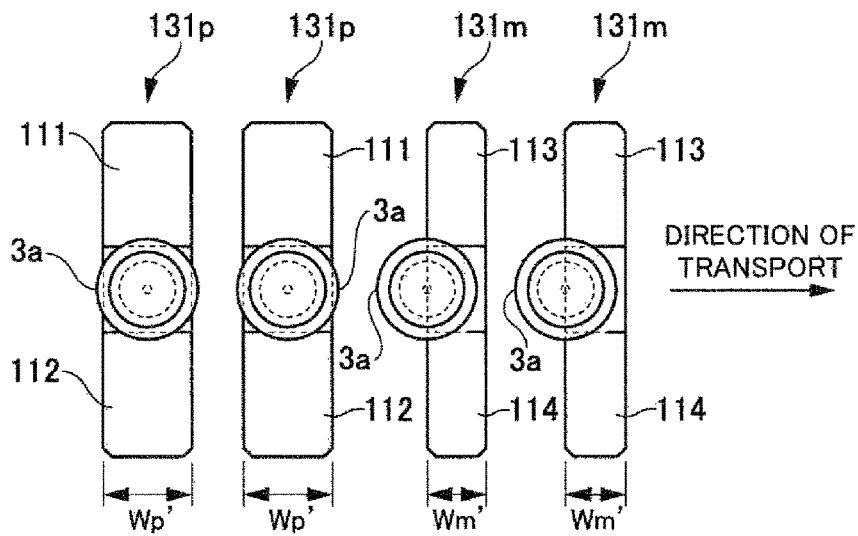
FIG. 22 illustrates first magnetic generation parts and second magnetic generation parts according to a third embodiment of the present invention.

FIG. 22 illustrates a first magnetic generation part and a second magnetic generation part according to a third embodiment of the present invention. In the third embodiment, main magnetic collection is performed in accordance with the second embodiment but on two reaction vessels 3a at a time.

As illustrated in FIG. 22, two second magnetic generation parts 131m for main magnetic collection are arranged in the vessel transport direction. The way how magnets in the second magnetic generation part 131m are assembled together is basically the same as that in the case of the second magnetic generation part 32m. Specifically, the second magnetic generation part 131m includes four magnets, but FIG. 22 illustrates only two magnets 113 and 114 on the upper side. These magnets 113 and 114 correspond to the magnets 91 and 95 of the second magnetic generation part 32m. Similarly to the second magnetic generation part 32m, the second magnetic generation part 131m includes a nonmagnetic member and a yoke (not illustrated).

The surface of each of the magnets 113 and 114 of each second magnetic generation part 131m facing the reaction vessel 3a has one of end portions in the vessel transport direction (on the upstream side in the vessel transport direction in FIG. 22) that is located adjacent to the center of the effective area of the reaction vessel 3a that has been transported to the magnetic collection position of the second magnetic generation part 131m. Thus, the magnetic particles contained in the liquid sample inside the reaction vessel 3a that have been preliminarily magnetically collected are magnetically and locally collected and held at a point in the main magnetic collection using strong magnetic forces produced at the end portions of each of the four magnets of the second magnetic generation part 131m, including the magnets 113 and 114. These two second magnetic generation parts 131m arranged side by side can replace the second magnetic generation part 32m that performs main magnetic collection on two reaction vessels 3a at a time.

Here, the second magnetic generation part 32m (see FIG. 7) according to the first embodiment may be replaced with two second magnetic generation parts 131m.

Instead of the configuration illustrated in FIG. 22, one first magnetic generation part 131p and one second magnetic generation part 131m may be provided. In this case, each of the preliminary magnetic collection and the main magnetic collection is performed in one cycle, which increases the analysis processing speed.

<Fourth Embodiment>

Figure 23:
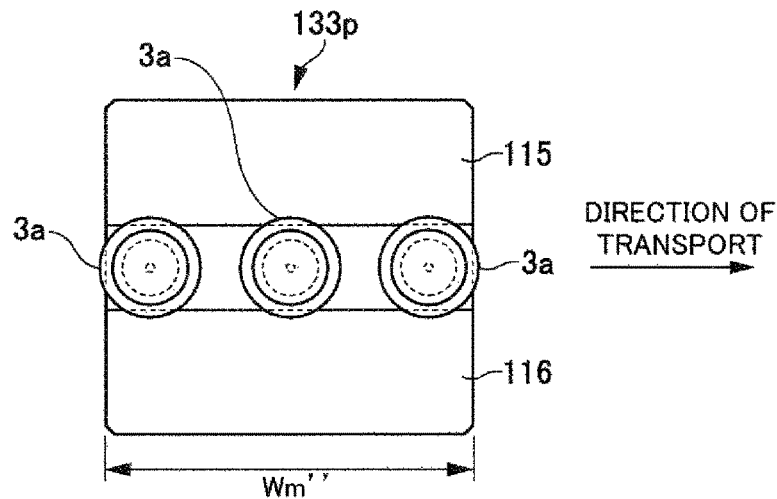
FIG. 23 illustrates a first magnetic generation part according to a fourth embodiment.

FIG. 23 illustrates a first magnetic generation part according to a fourth embodiment.

In the fourth embodiment, preliminary magnetic collection is performed on three reaction vessels 3a at a time.

Similarly to the first magnetic generation part 32p according to the first embodiment, a first magnetic generation part 133p includes four magnets. The way how the four magnets in the first magnetic generation part 133p are assembled together is basically the same as that in the case of the first magnetic generation part 32p. FIG. 23 illustrates only two magnets 115 and 116 on the upper side. These magnets 115 and 116 correspond to the magnets 71 and 75 of the first magnetic generation part 32p. Similarly to the first magnetic generation part 32p, the first magnetic generation part 131p includes a nonmagnetic member and a yoke (not illustrated).

The surface of each of the magnets 115 and 116 of the first magnetic generation part 133p facing the reaction vessels 3a has a width Wm" in the vessel transport direction that is as long as to cover effective areas of three reaction vessels 3a transported to the magnetic collection position of the first magnetic generation part 133p. Specifically, the width Wm" of each of the magnets 115 and 116 of the first magnetic generation part 133p is longer than or equal to the length obtained by adding the inner diameter of two reaction vessels 3a to the length equivalent to twice the arrangement pitch between three reaction vessels 3a transported to the magnetic collection position of the first magnetic generation part 133p. This configuration allows each of magnets of the first magnetic generation part 133p, including the magnets 115 and 116, to exert its magnetic force over the entirety of the liquid sample inside the three reaction vessels 3a. The magnetic particles widely dispersed in the liquid sample inside each reaction vessel 3a are thus roughly collected at a single point, as in the case of the first embodiment. In addition, three cycles of magnetic collection are performed on one reaction vessel 3a, so that a sufficiently large magnetic collection effect can be obtained.

Similarly to the first magnetic generation part 133p, the second magnetic generation part used for main magnetic collection may perform magnetic collection on three reaction vessels 3a at a time. In this case, the centers of the effective areas of both end reaction vessels among the three reaction vessels 3a are located adjacent to both end portions of the magnets, so that the effects the same as those in the case of the first embodiment can be obtained.

<Fifth Embodiment>

Figure 24:
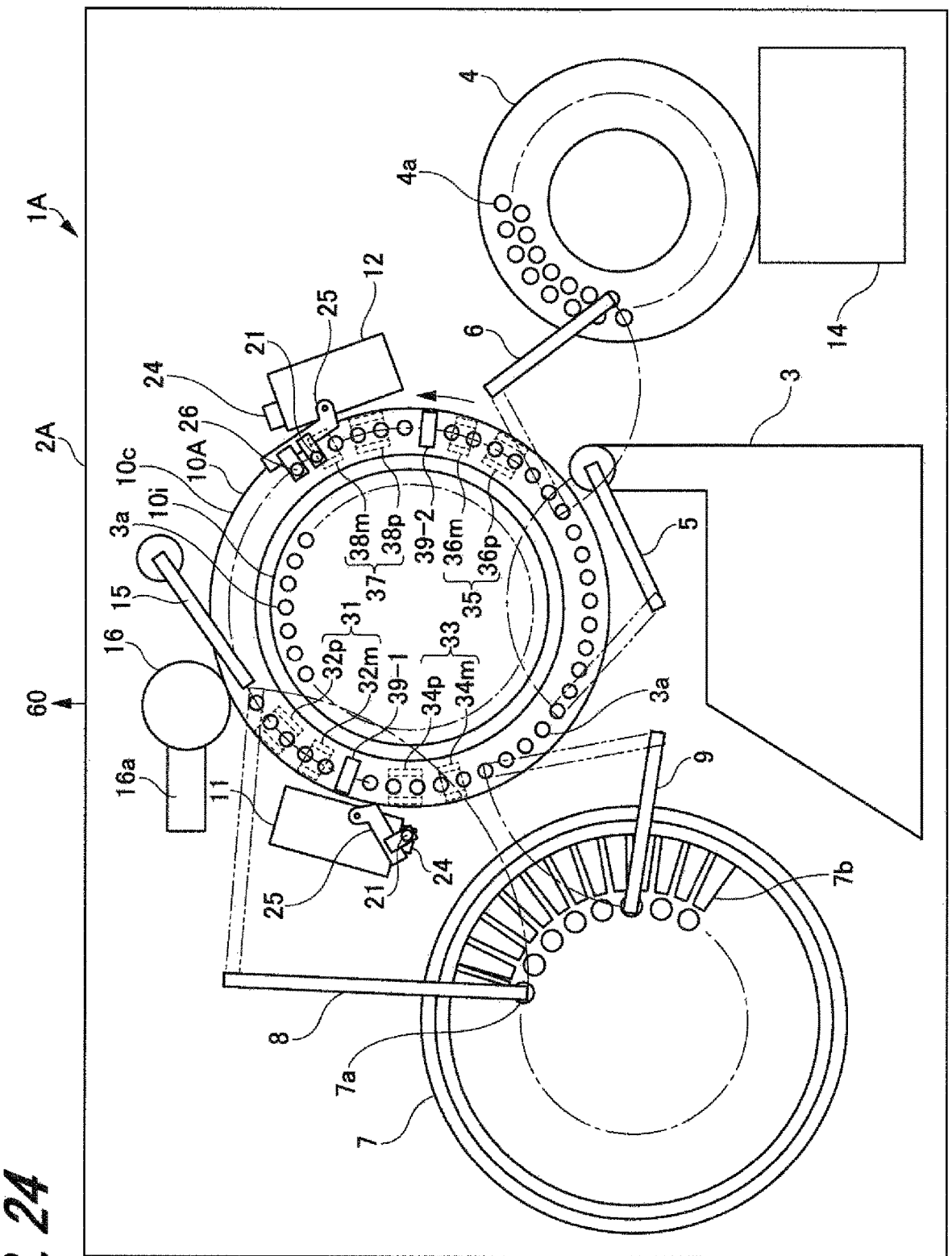
FIG. 24 is a schematic diagram of a configuration of an automatic analysis device according to a fifth embodiment.

FIG. 24 is a schematic configuration diagram of an automatic analysis device 1A according to a fifth embodiment.

The automatic analysis device 1A includes a measuring device 2A including an immuno-enzyme reaction unit 10A.

The immuno-enzyme reaction unit 10A includes an outer turntable 10c and an inner turntable 10i, disposed on the inner side of the outer turntable 10c. As in the case of the first embodiment, a first magnetic generation part and a second magnetic generation part for a BF separation step are disposed on the lower layer of the outer turntable 10c. The inner turntable 10i may include a stirring mechanism. The measuring device 2A having this configuration performs a primary immunoreaction operation at the inner turntable 10i. Each reaction vessel 3a that has been subjected to the primary immunoreaction operation is shifted to a predetermined position of the outer turntable 10c by an arm (reaction vessel shifting mechanism). The measuring device 2A then performs a primary BF separation operation, a secondary immunoreaction operation, a secondary BF separation operation, and an enzyme reaction operation at the outer turntable 10c.

Thus far, embodiments of the present invention have been described, but the present invention is not limited to the above-described embodiments. The present invention includes other embodiments and application examples within a scope not departing from the spirit of the invention described in the scope of the appended claim.

For example, the above-described embodiments specifically describe the configurations of devices and systems in detail for easy understanding of the present invention. The present invention is thus not necessarily limited to embodiments including all the components described above. At least one of the components in a certain embodiment is replaceable with another component. Alternatively, another component may be added to a configuration of a certain embodiment.

For example, the diameter or other parameters of the immuno-enzyme reaction unit 10 or 10A varies depending on the device configuration (particularly, reaction time or processing speed) according to each embodiment described above. Thus, the arrangement of the magnets in each magnetic generation part or the flow of the reaction vessels is not necessarily limited to any of these examples.

Each embodiment described above includes permanent magnets for use as the magnets 71, 72, 75, and 76 for preliminary magnetic collection and the magnets 91, 92, 95, and 96 for main magnetic collection. Instead, electromagnets may be used. The measuring device 2 includes, for example, a current source, which is not illustrated and which produces electric currents fed to the magnets 71, 72, 75, and 76 and the magnets 91, 92, 95, and 96 formed of electromagnets. The current source feeds electric currents to the magnets 71, 72, 75, and 76 and the magnets 91, 92, 95, and 96 under the control of the control portion 51 (FIG. 3). This configuration is capable of controlling whether each of the magnets 71, 72, 75, and 76 and the magnets 91, 92, 95, and 96 is to produce a magnetic field.

REFERENCE SIGNS LIST 1 automatic analysis device
2 measuring device
3a reaction vessel
10 immuno-enzyme reaction unit
11 first BF separation unit
12 second BF separation unit
21 nozzle
24 washing bath
31, 35 first-half magnetic collection mechanism
33, 37 second-half magnetic collection mechanism
32p, 34p, 36p, 38p first magnetic generation part (for preliminary magnetic collection)
32m, 34m, 36m, 38m second magnetic generation part (for main magnetic collection)
49d groove
71, 72, 75, 76 magnet
91, 92, 95, 96 magnet
60 controlling device
61 control portion

The invention claimed is:

1. An automatic analysis device that analyzes an intended substance contained in a sample using a reagent containing magnetic particles, the device comprising:
  a vessel transport portion in which vessels are disposed, the vessel transport portion transporting the vessels along a path, each of the vessels holding a liquid sample containing the sample and the reagent containing the magnetic particles;
  a first magnetic generation part disposed on the path and including at least one pair of preliminary-magnetic-collection magnets that magnetically collect the magnetic particles in the liquid sample inside each of the vessels that has been transported to a magnetic collection position of the first magnetic generation part, the pair of preliminary-magnetic-collection magnets being arranged opposite to each other with the vessels interposed therebetween;
  a second magnetic generation part disposed on the path downstream from the first magnetic generation part, the second magnetic generation part including at least one pair of main-magnetic-collection magnets that magnetically collect the magnetic particles in the liquid sample that have been magnetically collected by the first magnetic generation part, the liquid sample being held inside each vessel that has been transported to a magnetic collection position of the second magnetic generation part, and the pair of main-magnetic-collection magnets being arranged opposite to each other with the vessels interposed therebetween;
  a separation and washing portion that separates a component containing the magnetic particles and that washes an inside of each vessel while the magnetic particles are magnetically collected inside the vessel by the second magnetic generation part; and
  a luminescence measurement part that measures, using photon counting, light emission phenomena caused by an immune complex and a chemiluminescent substrate,
  wherein a surface of the preliminary-magnetic-collection magnet of the first magnetic generation part facing the vessels has a width in a vessel transport direction that is as long as to cover an area corresponding to a liquid sample volume in the vessels that have been transported to the magnetic collection position of the first magnetic generation part, and a surface of the main-magnetic-collection magnet of the second magnetic generation part facing the vessels has an end in the vessel transport direction that corresponds substantially to a center of the area corresponding to the liquid sample volume in the vessels that have been transported to the magnetic collection position of the second magnetic generation part,
  wherein the first magnetic generation part includes a first pair of a first magnet and a second magnet for use as the at least one preliminary-magnetic-collection magnet, the first magnet and the second magnet are arranged so as to face each other vertically and each have a first magnetic pole and a second magnetic pole arranged in a direction that is horizontal and that is perpendicular to the vessel transport direction, and the first and second magnetic poles of the first magnet and the first and second magnetic poles of the second magnet are arranged opposite to one another in the direction that is horizontal and that is perpendicular to the vessel transport direction, and wherein the second magnetic generation part includes a first pair of a third magnet and a fourth magnet for use as the at least one main-magnetic-collection magnet, the third magnet and the fourth magnet are arranged so as to face each other vertically and each have a first magnetic pole and a second magnetic pole arranged in a direction that is horizontal and that is perpendicular to the vessel transport direction, and the first and second magnetic poles of the third magnet and the first and second magnetic poles of the fourth magnet are arranged opposite to one another in the direction that is horizontal and that is perpendicular to the vessel transport direction.

2. The automatic analysis device according to claim 1, wherein each of the first magnetic generation part and the second magnetic generation part magnetically collects the magnetic particles in the liquid sample inside two of the vessels at a time, wherein the preliminary-magnetic-collection magnet of the first magnetic generation part has a width in the vessel transport direction that is longer than or equal to a length obtained by adding an inner diameter of two of the vessels to a distance between two of the vessels that have been transported to the magnetic collection position of the first magnetic generation part, and the main-magnetic-collection magnet of the second magnetic generation part has a width in the vessel transport direction that is equal to a distance between radial centers of two vessels that have been transported to the magnetic collection position of the second magnetic generation part.

3. The automatic analysis device according to claim 1, wherein the first magnetic generation part further includes a second pair of the first magnet and the second magnet on an opposite side of the first pair of the first magnet and the second magnet across the path, and wherein the second magnetic generation part further includes a second pair of the third magnet and the fourth magnet on an opposite side of the first pair of the third magnet and the fourth magnet across the path.

4. The automatic analysis device according to claim 1, wherein the first magnet, the second magnet, the third magnet, and the fourth magnet are each formed from a permanent magnet.

5. The automatic analysis device according to claim 1, wherein the first magnet, the second magnet, the third magnet, and the fourth magnet are each formed from an electromagnet and whether each magnet is to produce a magnetic field is controlled.

6. A separation and washing method for separating and washing a component containing magnetic particles with an automatic analysis device that analyzes an intended substance contained in a sample using a reagent containing magnetic particles, the method comprising:

a step of transporting vessels along a path using a vessel transport portion in which the vessels are disposed, the vessels each holding a liquid sample containing the sample and the reagent containing the magnetic particles;

a step of magnetically collecting, using a first magnetic generation part, the magnetic particles in the liquid sample inside each of the vessels that has been transported to a magnetic collection position of the first magnetic generation part, the first magnetic generation part being disposed on the path and including at least one preliminary-magnetic-collection magnet;

a step of magnetically collecting, using a second magnetic generation part, the magnetic particles in the liquid sample that have been magnetically collected by the first magnetic generation part inside each of the vessels that has been transported to a magnetic collection position of the second magnetic generation part, the second magnetic generation part being disposed on the path downstream from the first magnetic generation part, the second magnetic generation part including at least one main-magnetic-collection magnet;

a step of separating a component containing the magnetic particles and washing an inside of each vessel using a separation and washing portion while the magnetic particles are magnetically collected inside the vessel by the second magnetic generation part; and a step of measuring, using photon counting, light emission phenomena caused by an immune complex and a chemiluminescent substrate, wherein a surface of the preliminary-magnetic-collection magnet of the first magnetic generation part facing the vessels has a width in a vessel transport direction that is as long as to cover an area corresponding to a liquid sample volume in the vessels that have been transported to the magnetic collection position of the first magnetic generation part, and a surface of the main-magnetic-collection magnet of the second magnetic generation part facing the vessels has an end in the vessel transport direction that corresponds substantially to a center of the area corresponding to the liquid sample volume in the vessels that have been transported to the magnetic collection position of the second magnetic generation part, wherein the first magnetic generation part includes a first pair of a first magnet and a second magnet for use as the at least one preliminary-magnetic-collection magnet, the first magnet and the second magnet are arranged so as to face each other vertically and each have a first magnetic pole and a second magnetic pole arranged in a direction that is horizontal and that is perpendicular to the vessel transport direction, and the first and second magnetic poles of the first magnet and the first and second magnetic poles of the second magnet are arranged opposite to one another in the direction that is horizontal and that is perpendicular to the vessel transport direction, and wherein the second magnetic generation part includes a first pair of a third magnet and a fourth magnet for use as the at least one main-magnetic-collection magnet, the third magnet and the fourth magnet are arranged so as to face each other vertically and each have a first magnetic pole and a second magnetic pole arranged in a direction that is horizontal and that is perpendicular to the vessel transport direction, and the first and second magnetic poles of the third magnet and the first and second magnetic poles of the fourth magnet are arranged opposite to one another in the direction that is horizontal and that is perpendicular to the vessel transport direction.

* * * * *

UNITED STATES PATENT AND TRADEMARK OFFICE
CERTIFICATE OF CORRECTION

| | | |
|---|---|---|
| PATENT NO. | : 10,562,039 B2 | Page 1 of 1 |
| APPLICATION NO. | : 15/520228 | |
| DATED | : February 18, 2020 | |
| INVENTOR(S) | : Mizuki Nakamura | |

It is certified that error appears in the above-identified patent and that said Letters Patent is hereby corrected as shown below:

On the Title Page

Item (73), Column 1, Line 1, delete "Fujirbio Inc.," and insert --Fujirebio Inc.,--

Signed and Sealed this
Twelfth Day of May, 2020

Andrei Iancu
*Director of the United States Patent and Trademark Office*